(12) United States Patent
Yamanaka et al.

(10) Patent No.: US 10,321,812 B2
(45) Date of Patent: Jun. 18, 2019

(54) MEDICAL INSTRUMENT AND MEDICAL SYSTEM

(71) Applicant: OLYMPUS CORPORATION, Tokyo (JP)

(72) Inventors: Noriaki Yamanaka, Tokyo (JP); Keigo Takahashi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 280 days.

(21) Appl. No.: 15/248,704

(22) Filed: Aug. 26, 2016

(65) Prior Publication Data
US 2016/0360952 A1  Dec. 15, 2016

Related U.S. Application Data

(63) Continuation of application No. PCT/JP2015/053452, filed on Feb. 9, 2015.

(30) Foreign Application Priority Data

Feb. 28, 2014 (JP) .................... 2014-038277

(51) Int. Cl.
*A61B 1/00* (2006.01)
*A61B 1/005* (2006.01)
(Continued)

(52) U.S. Cl.
CPC ........ *A61B 1/0057* (2013.01); *A61B 1/00006* (2013.01); *A61B 1/0016* (2013.01); *A61B 1/00045* (2013.01); *A61B 1/0052* (2013.01); *A61B 1/00133* (2013.01); *A61B 1/018* (2013.01); *A61B 1/04* (2013.01); *A61B 1/06* (2013.01); *A61B 17/29* (2013.01); *A61B 34/37* (2016.02); *A61B 2017/003* (2013.01); *A61B 2017/00017* (2013.01);
(Continued)

(58) Field of Classification Search
CPC ..... A61B 1/0057; A61B 1/00133; A61B 1/04; A61B 1/06; A61B 1/00045; A61B 1/0052; A61B 1/00006; A61B 1/0016; A61B 34/37; A61B 2090/0812
USPC .................................................. 600/144, 149
See application file for complete search history.

(56) References Cited

U.S. PATENT DOCUMENTS 5,354,297 A   10/1994   Avitall
2004/0138530 A1   7/2004   Kawai et al.
(Continued)

FOREIGN PATENT DOCUMENTS

CN   102573599 A   7/2012
CN   102770060 A   11/2012
(Continued)

OTHER PUBLICATIONS

Extended Supplementary European Search Report dated Oct. 9, 2017 received in 15754826.4.
International Search Report dated Apr. 21, 2015 issued in corresponding International Patent Application No. PCT/JP2015/053452.

*Primary Examiner* — Timothy J Neal
(74) *Attorney, Agent, or Firm* — Scully, Scott, Murphy & Presser, P.C.

(57) ABSTRACT

The medical instrument 1 includes a wire 5, a flexible sheath 6 through which the wire 5 is inserted, a wire driving unit 4 for driving the wire 5, a passive unit 2 that is put into operation as the wire 5 is driven, a sheath pulling unit 14, 17, 21, 51, and a sheath lock unit 12, 13, 20 for locking movement of the sheath 6.

16 Claims, 22 Drawing Sheets

(51) Int. Cl.
   *A61B 17/29* (2006.01)
   *A61B 34/37* (2016.01)
   *A61B 1/018* (2006.01)
   *A61B 1/04* (2006.01)
   *A61B 1/06* (2006.01)
   *A61B 34/00* (2016.01)
   *A61B 90/00* (2016.01)
   *A61B 34/30* (2016.01)
   *A61B 17/00* (2006.01)

(52) U.S. Cl.
   CPC ............ *A61B 2017/0034* (2013.01); *A61B 2017/00327* (2013.01); *A61B 2017/2905* (2013.01); *A61B 2034/301* (2016.02); *A61B 2034/715* (2016.02); *A61B 2090/061* (2016.02); *A61B 2090/064* (2016.02); *A61B 2090/0811* (2016.02); *A61B 2090/0812* (2016.02)

(56) References Cited

U.S. PATENT DOCUMENTS

| | | |
|---|---|---|
| 2007/0250113 A1 | 10/2007 | Hegeman et al. |
| 2008/0319260 A1 | 12/2008 | Murakami et al. |
| 2009/0030273 A1 | 1/2009 | Murakami |
| 2010/0331820 A1 | 12/2010 | Prisco et al. |
| 2011/0106141 A1 | 5/2011 | Nakamura |
| 2011/0282153 A1 | 11/2011 | Ueki |
| 2011/0295063 A1 | 12/2011 | Umemoto et al. |
| 2012/0046522 A1 | 2/2012 | Naito |
| 2012/0071752 A1 | 3/2012 | Sewell et al. |
| 2013/0184528 A1 | 7/2013 | Onuki et al. |
| 2013/0274722 A1 | 10/2013 | Kostrzewski et al. |
| 2015/0313619 A1 | 11/2015 | Tadano et al. |

FOREIGN PATENT DOCUMENTS

| | | |
|---|---|---|
| CN | 103153159 A | 6/2013 |
| CN | 103565489 A | 2/2014 |
| EP | 2 687 164 A2 | 1/2014 |
| JP | S63-093904 U | 6/1988 |
| JP | 7-504834 A | 6/1995 |
| JP | 7-328024 A | 12/1995 |
| JP | 2001-258828 A | 9/2001 |
| JP | 2004-230201 A | 8/2004 |
| JP | 2009-000500 A | 1/2009 |
| JP | 2009-106697 A | 5/2009 |
| JP | 2009-112538 A | 5/2009 |
| JP | 2009-240763 A | 10/2009 |
| JP | 4856289 B2 | 1/2012 |
| JP | 2012-531943 A | 12/2012 |
| JP | 2014-090800 A | 5/2014 |

MEDICAL INSTRUMENT AND MEDICAL SYSTEM

CROSS-REFERENCE TO RELATED APPLICATIONS

This application is a continuation claiming priority on the basis of Japan Patent Application No. 2014-038277 applied in Japan on Feb. 28, 2014 and based on PCT/JP2015/053452 filed on Feb. 9, 2015. The contents of both the PCT application and the Japan Application are incorporated herein by reference.

BACKGROUND OF THE INVENTION AND RELATED ART STATEMENT

The present invention relates to a medical instrument and a medical system that are each inserted through the body cavity of a patient for surgical operation to view, and apply treatments or the like to, the interior of the patient's body cavity.

There has been a medical instrument widely used in the art, in which an elongate insert unit is inserted into the body cavity of a patient and a wire or the like is used to haul the distal end of the insert unit to view, and apply treatments to, organs in the body cavity.

JP(A) 2009-106697 shows that a coil pipe is held in a given length for incorporation into an endoscope in a preferable state and improvements in the operability by an operating wire.

With the technology set forth in JP(A) 2009-106697, however, it is still impossible to take up slack in a sheath for the purpose of being well compatible with the shape of a flexible portion when there is a change in the shape of the flexible portion during treatment, because a sheath location has been fixed in place upon assembling.

SUMMARY OF INVENTION

The medical instrument according to one embodiment includes
  a wire,
  a flexible sheath through which the wire is inserted,
  a wire driving unit for driving the wire,
  a passive unit that is put into operation as the wire is driven,
  a sheath pulling unit for pulling the sheath, and
  a sheath lock unit for locking movement of the sheath.

According to one embodiment, there is a medical system provided that the medical instrument is an endoscope including a viewing optical system, an imaging device and a lighting optical system, and the passive unit is defined by a distal-end portion of the endoscope to which one end of the wire is attached and a flexible portion through which the wire and the sheath are inserted, the medical system further includes an operating unit for driving the wire driving unit, to which the other end of the wire is attached, to put the distal-end portion and the flexible portion into operation, a display unit for displaying an image acquired through the endoscope, and a system control unit for putting the operating unit into operation thereby controlling the endoscope and permitting the image acquired through the endoscope to be displayed on the display unit.

DESCRIPTION OF EMBODIMENTS

Some embodiments are now explained.

Figure 1:
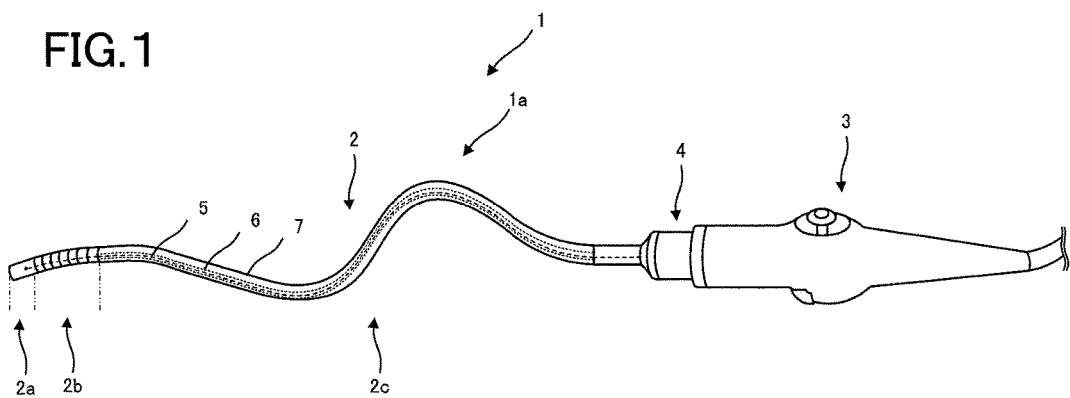
FIG. 1 is a schematic view of one example of the medical instrument according to one embodiment.

FIG. 1 is a schematic view of the medical instrument 1 according to one embodiment.

One example of the medical instrument 1 according to the embodiment described herein includes an endoscope 1a including at least an insert unit 2, an operating unit 3, a wire driving unit 4, a wire 5 and a sheath 6. The medical instrument 1 has the insert unit 2 on a distal-end side and the operating unit 3 on a proximal-end side. Inserted through the body cavity, the insert unit 2 includes, in order from the distal-end side, a distal-end portion 2a, a curving portion 2b and a flexible portion 2c. The flexible portion 2c is covered on its outer circumference with an outer cover 7. Note here that the curving portion 2b may be dispensed with or, alternatively, a joint portion may be used instead of the curving portion 2b. Referring to the operating unit 3, a wire 5 is driven by the wire driving unit 4 for operation of the curving state of the curving portion 2b and the orientation of the distal-end portion 2a. The operating unit 3 and wire driving unit 4 are connected to a power source, a controller or the like (not shown) by way of cables. The insert unit 2 and driving unit 4 are detachable from each other or, alternatively, the wire driving unit 4 may be built in the operating unit 3.

Figure 2:
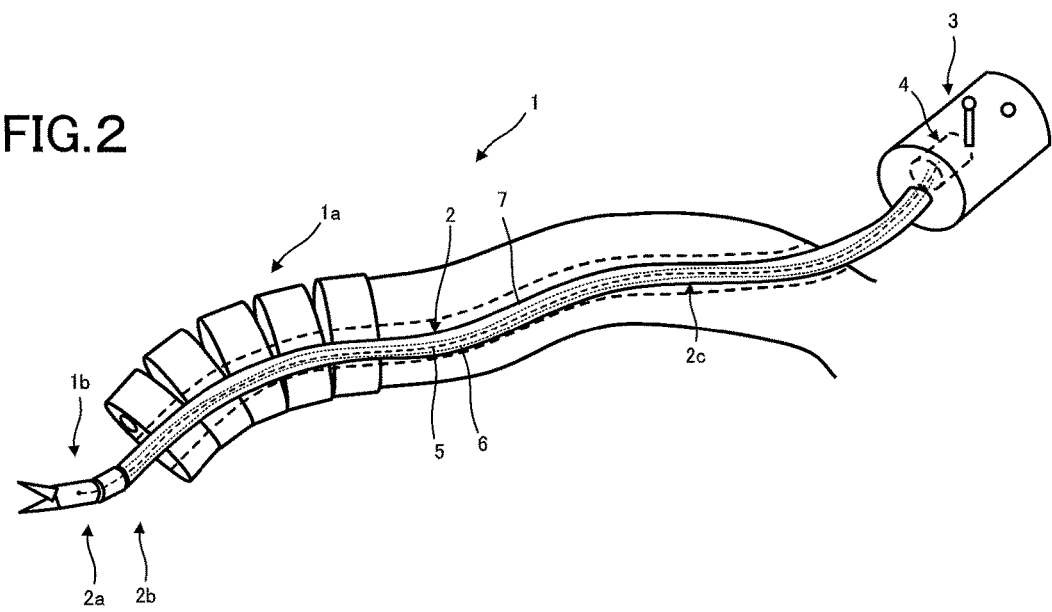
FIG. 2 is a schematic view of another example of the medical instrument according to the embodiment.

FIG. 2 is a schematic view of another example of the medical instrument 1 according to the embodiment described herein.

Another example of the medical instrument 1 according to the embodiment described herein includes a treatment tool 1b including at least an insert unit 2, an operating unit 3, a wire driving unit 4, a wire 5 and a sheath 6, and is used while inserted inside the endoscope 1a. The medical instrument 1 has the insert unit 2 on a distal-end side and the operating unit 3 on a proximal-end side. Inserted together with the endoscope through the body cavity, the insert unit 2 includes, in order from the distal-end side, a distal-end portion 2a, a curving portion 2b and a flexible portion 2c. The flexible portion 2c is covered on its outer circumference with an outer cover 7. Note here that the curving portion 2b may be dispensed with or, alternatively, a joint portion may be used instead of the curving portion 2b. Referring to the operating unit 3, a wire 5 is driven by the wire driving unit 4 for operation of the curving state of the curving portion 2b and the orientation of the distal-end portion 2a. Note here that a treatment tool such as a pair of forceps may be operated by the operating unit 3. The operating unit 3 and wire driving unit 4 are connected to a power source, a controller or the like (not shown) by way of cables. The insert unit 2 and wire driving unit 4 are detachable from each other or, alternatively, the wire driving unit 4 may be built in the operating unit 3.

In the examples shown in FIGS. 1 and 2, one end of the wire 5 is attached to the distal-end portion 2b and the other end of the wire 5 is coupled to the wire driving unit 4. The sheath 6 is mounted inside the outer cover 7, and there is the wire 5 inserted inside the sheath 6.

Figure 3A:
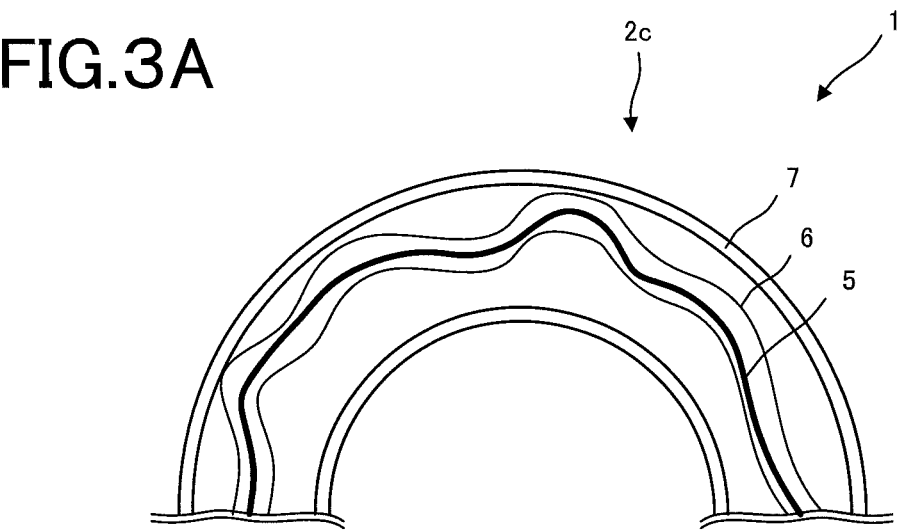
FIGS. 3A and 3B are a schematic view of one example of the flexible portion of the medical instrument according to one embodiment.
Figure 3B:
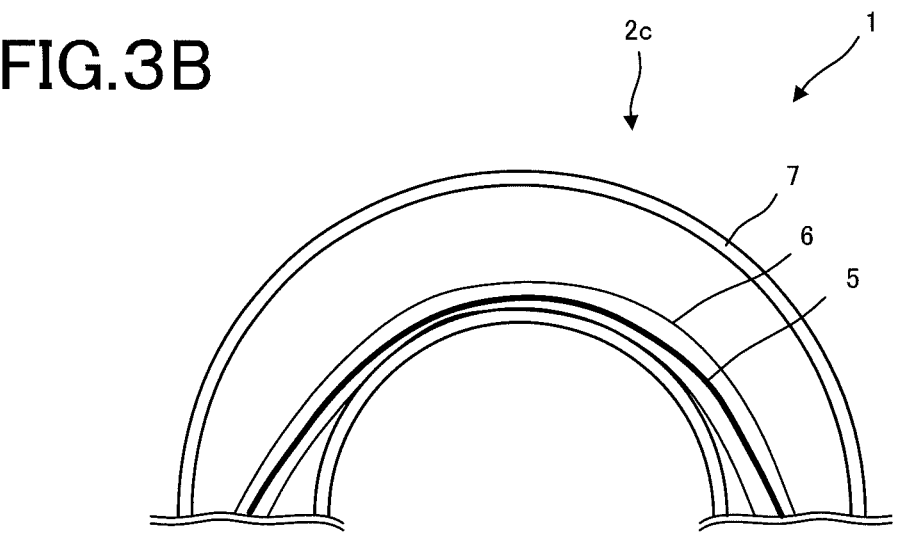

FIGS. 3A and 3B are a schematic view of one example of the flexible portion 2c of the medical instrument 1 according to the embodiment described herein: FIG. 3A shows that the sheath 6 and wire 5 are slacking with respect to the outer cover 7 over the flexible portion 2c and FIG. 3B shows that the sheath 6 and wire 5 are pulled from the state of FIG. 3A.

The flexible portion 2c includes the outer cover 7, the sheath 6 inserted inside the outer cover 7 and the wire 5 inserted inside the sheath 6. The flexible portion 2c takes on various shapes depending on conditions under which the medical instrument 1 is used.

Referring to the medical instrument 1 according to the embodiment described herein, when the flexible portion 2c curves and the sheath 6 slacks as shown in FIG. 3A, the sheath 6 is pulled as shown in FIG. 3B after the shape of the flexible portion 2c is fixed so that the sheath 6 is fixed in such a way as to route through the shortest path within the outer cover 7. Then, the wire 5 is driven in the state shown in FIG. 3B, leading not only to an increased resistance to compression and a decreased friction, but also to high responsiveness. There is no or little change in performance characteristics depending on shape changes, which results in ease of control.

The sheath pulling mechanism 10 according to the first embodiment used with the medical instrument 1 shown in FIG. 1 or 2 is now explained.

Figure 4A:
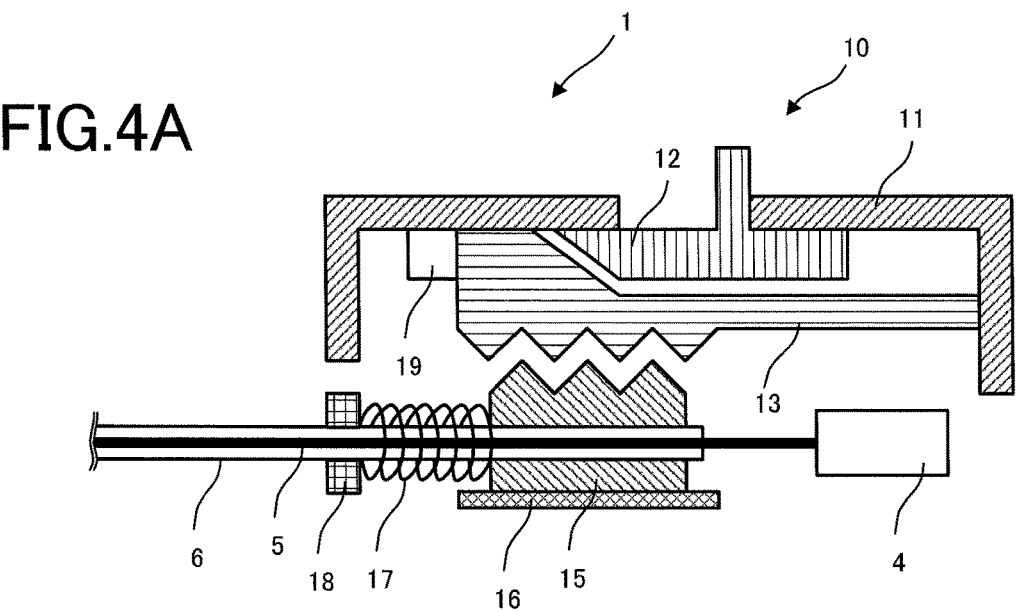
FIGS. 4A and 4B are a schematic view of the sheath pulling mechanism for the medical instrument according to the first embodiment.
Figure 4B:
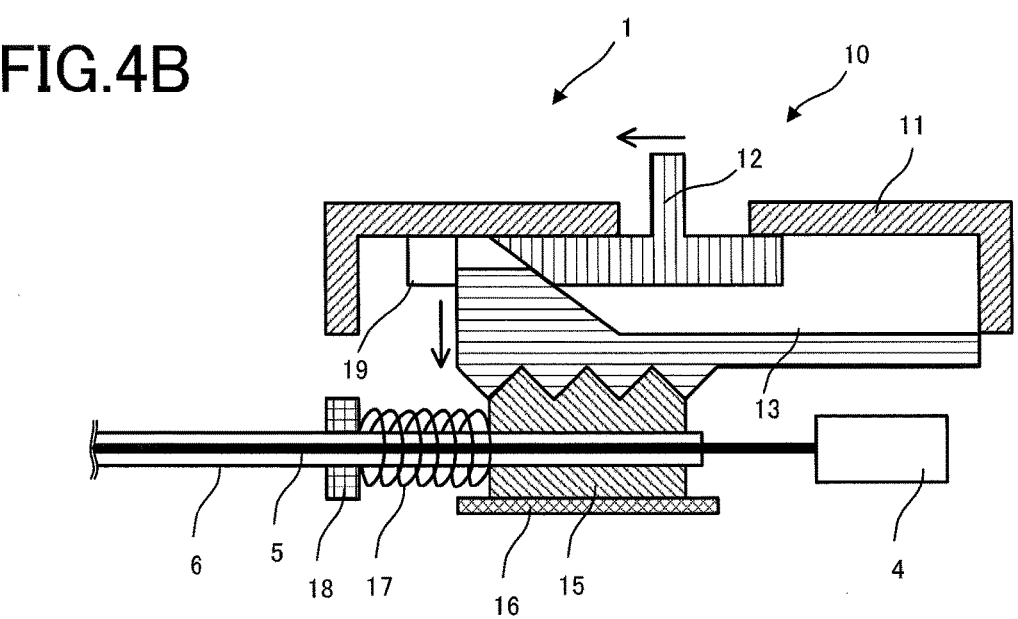

FIGS. 4A and 4B are a schematic view of the sheath pulling mechanism 10 for the medical instrument 1 according to the first embodiment: FIG. 4A is a schematic view of the sheath pulling mechanism 10 according to the first embodiment before movement and FIG. 4B is a schematic view of the sheath pulling mechanism 10 according to the first embodiment after movement.

The sheath pulling mechanism 10 for the medical instrument 1 according to the first embodiment includes a case 11, a sheath lock-operation unit 12, a sheath lock member 13, a wire driving unit 4, a sheath support member 15, a sheath support member guide 16, a biasing member 17, a through-the-sheath unit 18 and a lock detection unit 19. Note here that the case 11 may also serve as the operating unit 3 shown in FIG. 1 or 2, and the sheath support member guide 16 and through-the-sheath unit 18 may be fixed to the outer cover 7 over the flexible portion 2c shown in FIGS. 3A and 3B or, alternatively, integrated with the case 11. In the first embodiment, the biasing member 17 such as a spring and sheath support member 15 form together a sheath pulling unit, and the sheath lock-operation unit 12 and sheath lock member 13 form together a sheath lock unit.

As shown in FIG. 4A, the sheath lock-operation unit 12 of the sheath pulling mechanism 10 may be operated from outside the case 11: it is capable of sliding in the first embodiment. The sheath lock member 13 is pressed by movement of the sheath lock-operation unit 12 to move toward the sheath support member 15. In the first embodiment, a portion of the slid sheath lock-operation unit 12 that tilts at a given angle is pressed on a portion of the sheath lock member 13 that tilts at a given angle to move the sheath lock member 13 toward the sheath support member 15.

The sheath support member 15 is previously fixed to the sheath 6 and supported in such a way as to be movable toward the sheath support member guide 16, and the sheath support member 15 is biased by the biasing member 17 toward the through-the-sheath unit 18 in a direction of pulling the sheath 6. In addition, the through-the-sheath unit 18 movably supports the sheath 6. Thus, the sheath 6 is constantly pulled toward the wire driving unit 4 side, so it is less slacking. The wire 5 is mounted on the wire driving unit 4.

Referring to the sheath pulling mechanism 10, the sheath lock-operation unit 12 is operated as shown in FIG. 4B for movement of the sheath lock member 13. The moving sheath lock member 13 gets in engagement with the sheath support member 15 and is locked. Thus, the sheath 6 maintains shape in a less slacking state shown in FIG. 4B. The lock detection unit 19 detects movement of the sheath lock member 13 thereby determining whether or not the sheath pulling mechanism 10 is locked in place.

Such sheath pulling mechanism 10 for the medical instrument 1 according to the first embodiment ensures that the sheath 6 can be fixed in a pulled state under constant tension simply by the operation by the operator of the sheath lock-operation unit 12 so that the sheath 6 can be held in a slack-free state.

The sheath pulling mechanism 10 for the medical instrument 1 according to the second embodiment is now explained.

Figure 5A:
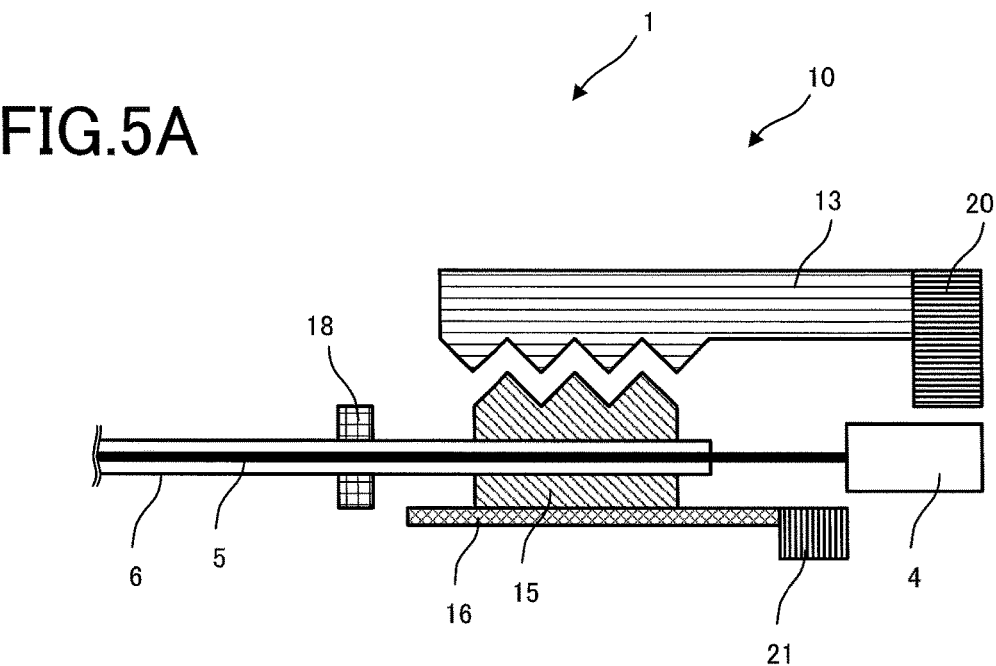
FIGS. 5A and 5B are a schematic view of the sheath pulling mechanism for the medical instrument according to the second embodiment.
Figure 5B:
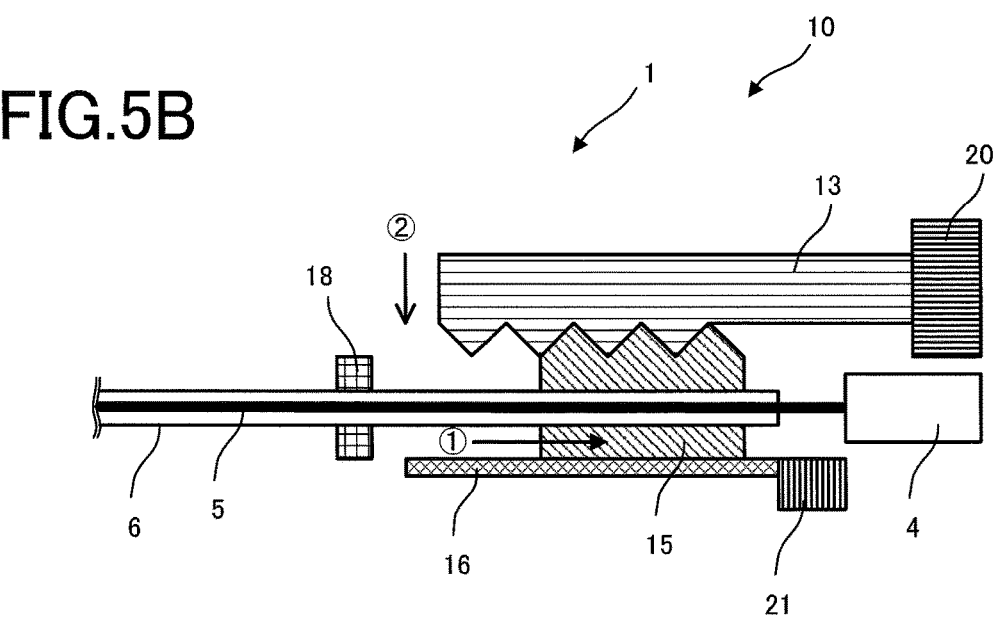

FIGS. 5A and 5B are a schematic view of the sheath pulling mechanism 10 for the medical instrument 1 according to the second embodiment: FIG. 5A is a schematic view of the sheath pulling mechanism 10 according to the second embodiment before movement and FIG. 5B is a schematic view of the sheath pulling mechanism 10 according to the second embodiment after movement.

The sheath pulling mechanism 10 for the medical instrument 1 according to the second embodiment includes a sheath lock member 13, a wire driving unit 4, a sheath support member 15, a sheath support member guide 16, a through-the-sheath unit 18, a sheath lock driving unit 20 and a sheath pulling driving unit 21. Note here that the sheath pulling mechanism 10 may be incorporated in the operating unit 3 shown in FIG. 1 or 2, and that the wire driving unit 4 may also serve as the wire driving unit 4 shown in FIG. 1 or 2. Further, the sheath support member guide 16 and through-the-sheath unit 18 may be fixed to the outer cover 7 over the flexible portion 2c shown in FIGS. 3A and 3B or, alternatively, integrated with the case 11. In the second embodiment, the sheath pulling driving unit 21 and sheath support member 15 form together a sheath pulling unit, and the sheath lock driving unit 20 and sheath lock member 13 form together a sheath lock unit.

As shown in FIG. 5A, the sheath lock member 13 in the sheath pulling mechanism 10 is driven by the sheath lock driving unit 20 such as an actuator in such a way as to be movable in a direction of coming into engagement with, and going away from, the sheath support member 15. The sheath support member 15 is previously fixed to the sheath 6, and mounted on the sheath support member guide 16 in such a way as to be movable in a direction of pulling, and getting back, the sheath 6 by the sheath pulling driving unit 21 such as an actuator. The wire 5 is detachably mounted on the wire driving unit 4.

The sheath pulling mechanism 10 is actuated as by a switch (not shown). First of all, the sheath support member 15 is moved by the sheath pulling driving unit 21 in a direction of pulling the sheath 6 to reduce the slack in the sheath 6. Then, the sheath lock driving unit 20 is driven to bring the sheath lock member 13 in engagement with the sheath support member 15, as shown in FIG. 5B, so that the sheath 6 maintains shape in a less slacking state. Note here that whether or not the sheath 6 is locked may be determined by detecting the driving state of the sheath lock driving unit 20 or, alternatively, by detecting the movement of the sheath lock member 13 as is the case with the lock detection unit 19 shown in FIGS. 4A and 4B.

With such sheath pulling mechanism 10 according to the second embodiment, it is possible to pull the sheath 6 under a constant tension and fix it in a slack-free shape.

The sheath pulling mechanism 10 for the medical instrument 1 according to the third embodiment is now explained.

Figure 6A:
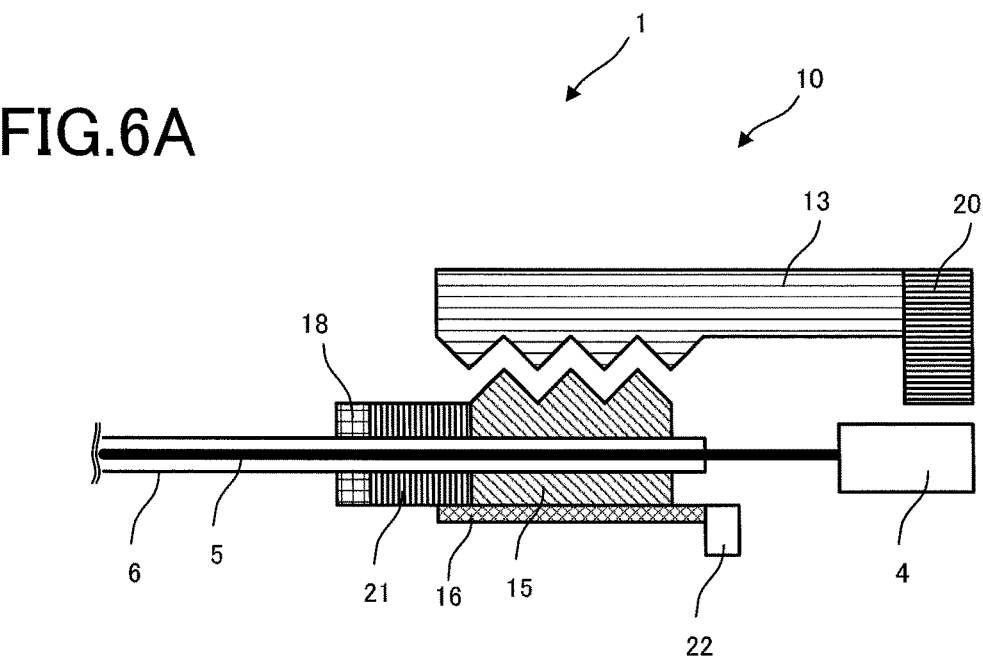
FIGS. 6A and 6B are a schematic view of the sheath pulling mechanism for the medical instrument according to the third embodiment.
Figure 6B:
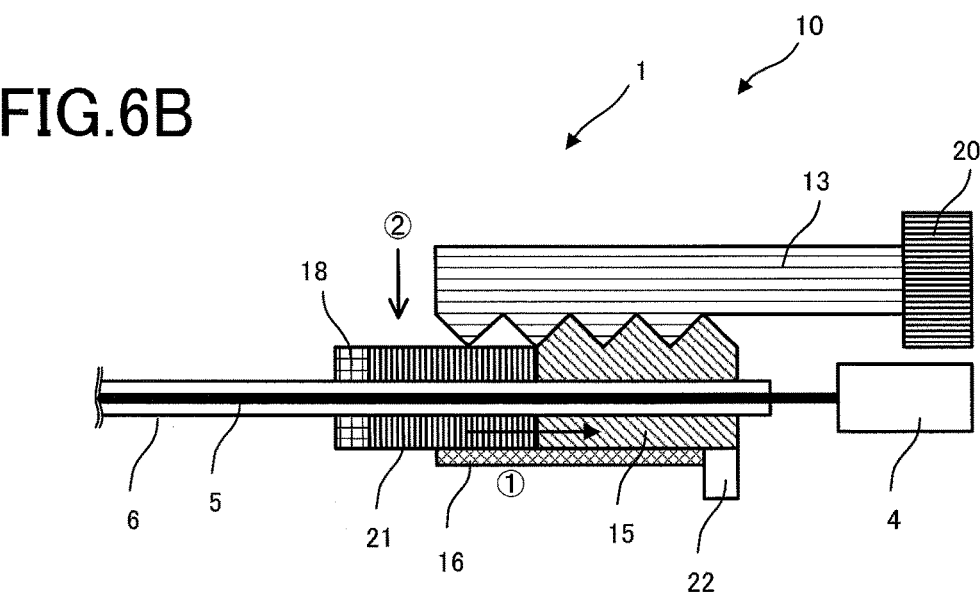
Figure 7:
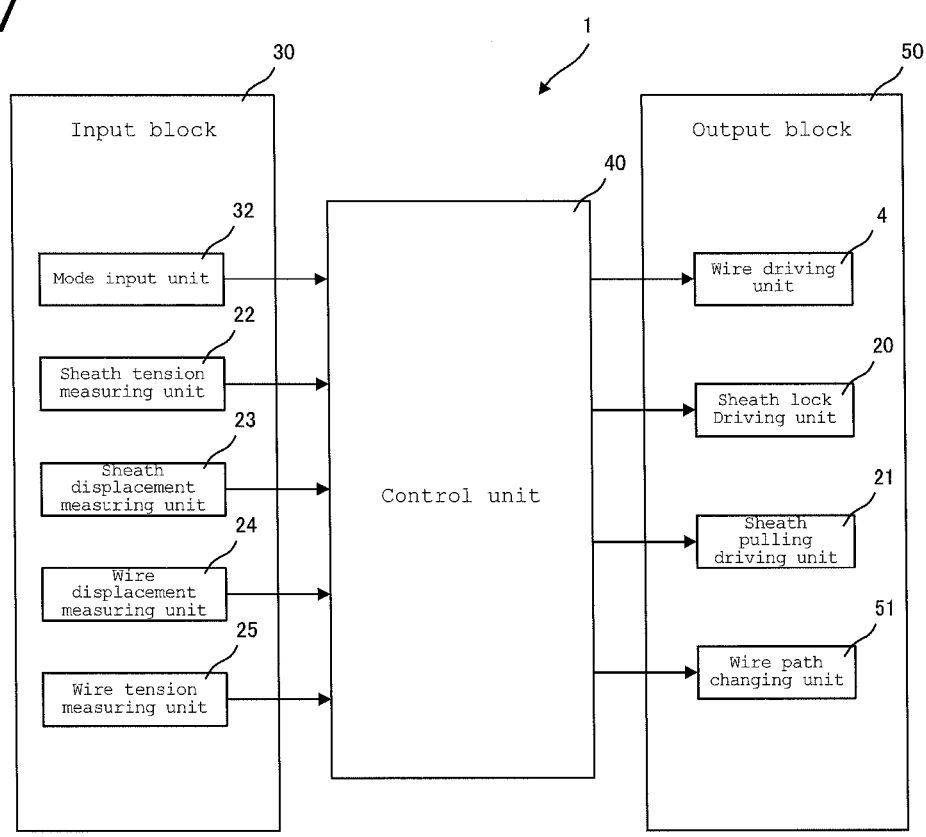
FIG. 7 is a control block diagram for the medical instrument according to the third embodiment.
Figure 8:
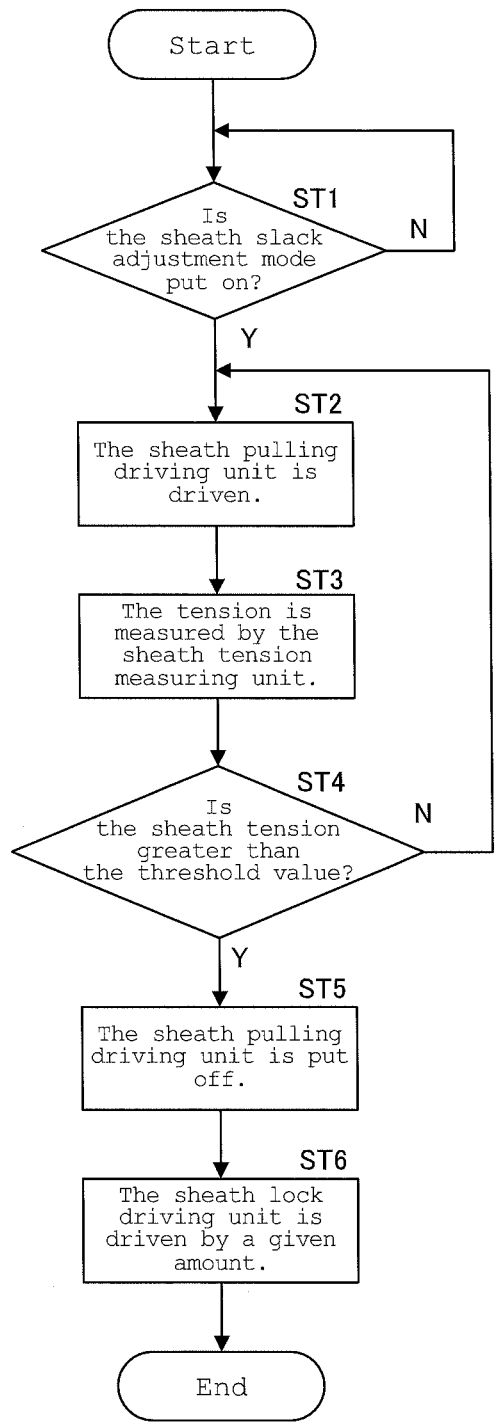
FIG. 8 is a control flowchart for the medical instrument according to the third embodiment.

FIGS. 6A and 6B are a schematic view of the sheath pulling mechanism 10 for the medical instrument 1 according to the third embodiment: FIG. 6A is a schematic view of the sheath pulling mechanism 10 according to the third embodiment before movement and FIG. 6B is a schematic view of the sheath pulling mechanism 10 according to the third embodiment after movement. FIG. 7 is a control block diagram for the medical instrument 1 according to the embodiment described herein, and FIG. 8 is a control flowchart for the medical instrument 1 according to the third embodiment.

As shown in FIGS. 6A and 6B, the sheath pulling mechanism 10 for the medical instrument 1 according to the third embodiment is a modification to the location of the sheath pulling driving unit 21 according to the second embodiment shown in FIGS. 5A and 5B. The sheath pulling mechanism 10 here additionally includes a sheath tension measuring unit 22. The rest of the structure will not be explained anymore because of being similar to that of the sheath pulling mechanism 10 for the medical instrument 1 according to the second embodiment. In the third embodiment, the sheath pulling driving unit 21 and sheath support member 15 form together a sheath pulling unit, and the sheath lock driving unit 20 and sheath lock member 13 define together a sheath lock unit.

In the sheath pulling mechanism 10 according to the third embodiment, as shown in FIG. 6A, the sheath pulling driving unit 21 is interposed between the through-the-sheath unit 18 and the sheath support member 15. The sheath support member 15 is previously fixed to the sheath 6, and mounted on the sheath support member guide 16 in such a way as to be movable in a direction of pulling, and getting back, the sheath 6 by the sheath pulling driving unit 21.

The medical instrument 1 according to the embodiment described herein includes such a control block as depicted in FIG. 7. However, it is not always necessary to use all of the units in the input 30 and output 50 blocks or units; at least some units may be used depending on structural requirements.

The third embodiment here includes a mode input unit 32 and sheath tension measuring unit 22 of the input block 30. The mode input unit 32 detects that a sheath slack adjustment mode for reducing the slack in the sheath 6 is put on, and enters the resultant signal into a control unit 40. The tension of the sheath 6 is measured by the sheath tension measuring unit 22 to enter the resultant measurement into the control unit 40.

A flow controlled by the control unit 40 for the medical instrument 1 according to the third embodiment is now explained.

In the medical instrument 1 according to the third embodiment, whether or not the sheath slack adjustment mode of the mode input unit 32 is put on is first determined in Step 1 (ST1). If the sheath slack adjustment mode being put on is not detected in Step 1, the processing then goes back to Step 1.

When detecting in Step 1 that the sheath slack adjustment mode is put on, the processing then goes to Step 2 in which the sheath pulling driving unit 21 is driven (ST2). Then, the processing goes to Step 3 in which the sheath tension is measured by the sheath tension measuring unit 22 (ST3).

Then, the processing goes to Step 4 in which it is determined whether or not the sheath tension measured by the sheath tension measuring unit 22 is greater than a predetermined threshold value (ST4). In Step 4, if the sheath tension is not greater than the predetermined threshold value, the processing then goes back to Step 2.

In Step 4, if the sheath tension is greater than the predetermined threshold value, the processing goes to Step 5 in which the sheath pulling driving unit 21 is put off (ST5). Subsequently, the processing goes to Step 6 in which the sheath lock driving unit 20 is driven by a given amount so that the sheath 6 is pulled, and locked and fixed in place (ST6), after which the control gets done.

With such sheath pulling mechanism 10 for the medical instrument 1 according to the third embodiment, it is possible to pull and fix the sheath 6 in place while measuring the sheath tension for precise correction of the slack in the sheath 6.

It is here to be noted that the sheath tension measuring unit 22 may be added to the construction of the medical instrument 1 according to the second embodiment shown in FIGS. 5A and 5B to implement control as is the case with the third embodiment.

The sheath pulling mechanism 10 for the medical instrument 1 according to the fourth embodiment is now explained.

Figure 9A:
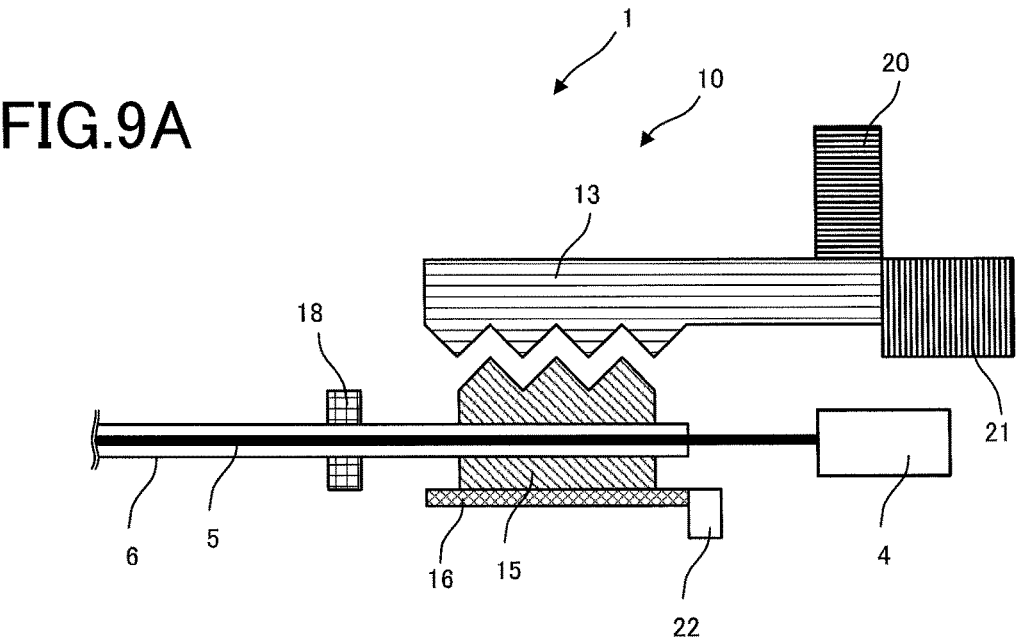
FIGS. 9A and 9B are a schematic view of the sheath pulling mechanism for the medical instrument according to the fourth embodiment.
Figure 9B:
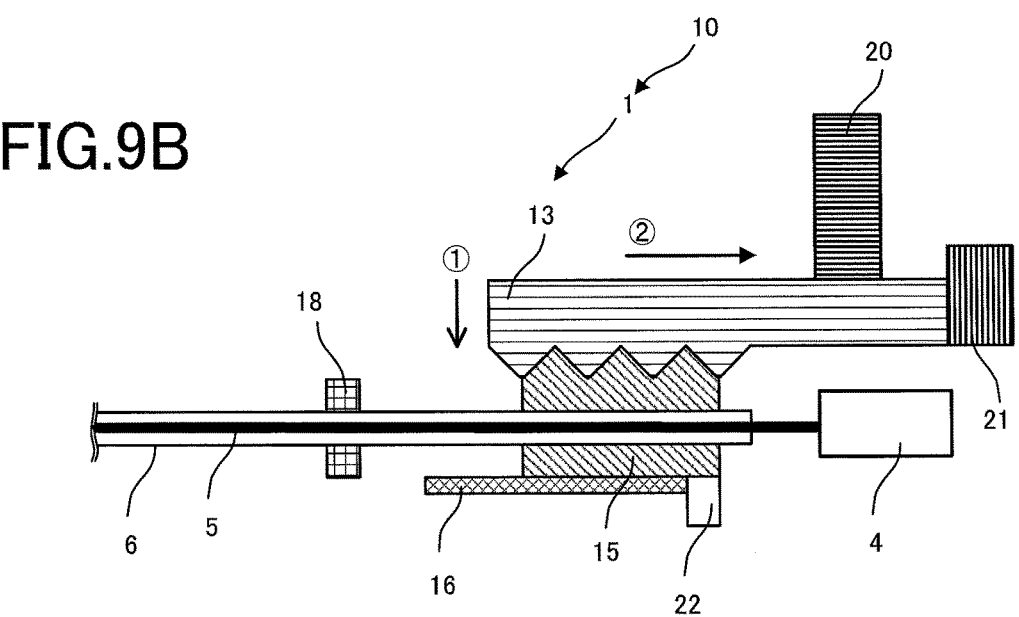
Figure 10:
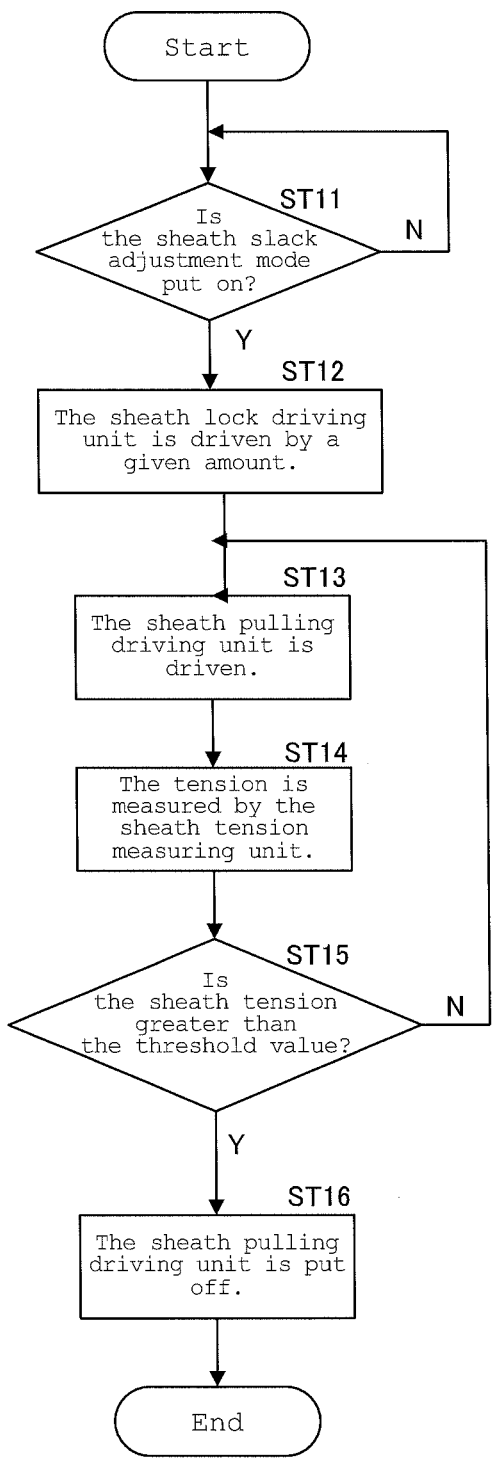
FIG. 10 is a control flowchart for the medical instrument according to the fourth embodiment.

FIGS. 9A and 9B are a schematic view of the sheath pulling mechanism 10 for the medical instrument 1 according to the fourth embodiment: FIG. 9A is a schematic view of the sheath pulling mechanism 10 according to the fourth embodiment before movement and FIG. 9B is a schematic view of the sheath pulling mechanism 10 according to the fourth embodiment after movement. FIG. 10 is a control flowchart for the medical instrument according to the fourth embodiment.

As shown in FIGS. 9A and 9B, the sheath pulling mechanism 10 for the medical instrument 1 according to the fourth embodiment is a modification to the location of the sheath lock driving unit 20 and sheath pulling driving unit 21 according to the third embodiment shown in FIGS. 6A and 6B. The rest of the structure will not be explained anymore because of being similar to that of the sheath pulling mechanism 10 for the medical instrument 1 according to the third embodiment. In the fourth embodiment, the sheath pulling driving unit 21 and sheath support member 15 form together a sheath pulling unit, and the sheath lock driving unit 20 and sheath lock member 13 define together a sheath lock unit.

In the sheath lock driving unit 20 of the sheath pulling mechanism 10 for the medical instrument 1 according to the fourth embodiment, as shown in FIG. 9A, the sheath lock member 13 is placed in such a way as to be movable in a direction of coming into engagement with, and going away from, the sheath support member 15, and the sheath pulling driving unit 21 is placed in such a way as to be movable in a direction of pulling the sheath 6 toward the sheath lock member 13 or getting back sheath 6. The sheath support member 15 is previously fixed to the sheath 6, and mounted on the sheath support member guide 16 in such a way as to be movable in a direction of pulling, and getting back, the sheath 6 as the sheath pulling driving unit 21 is driven.

The medical instrument 1 according to the fourth embodiment includes the mode input unit 32 and sheath tension measuring unit 22 out of the input block 30 forming a part of the control block shown in FIG. 7. The mode input unit 32 detects that the sheath slack adjustment mode of reducing the slack in the sheath 6 is put on, and enters the resultant signal into the control unit 40. The tension of the sheath 6 is measured by the sheath tension measuring unit 22 to enter the resultant measurement into the control unit 40.

A flow controlled by the control unit 40 for the medical instrument 1 according to the fourth embodiment is now explained.

In the medical instrument 1 according to the fourth embodiment, whether or not the sheath slack adjustment mode of the mode input unit 32 shown in FIGS. 6A and 6B is put on is firstly determined in Step 11 (ST11). In Step 11, when the sheath slack adjustment mode being put on is not detected, the processing then goes back to Step 11.

When detecting in Step 11 that the sheath slack adjustment mode is put on, the processing then goes to Step 12 in which the sheath lock driving unit 20 is driven by a given amount such that the sheath lock member 13 is in mesh with the sheath support member 15 (ST12).

Then, the processing goes to Step 13 in which the sheath pulling driving unit 21 is driven (ST13), and then goes to Step 14 in which the sheath tension is measured by the sheath tension measuring unit 22 (ST14).

Then, the processing goes to Step 15 in which it is determined whether or not the sheath tension measured by the sheath tension measuring unit 22 is greater than a predetermined threshold value (ST15). In Step 15, if the sheath tension is not greater than the predetermined threshold value, the processing then goes back to Step 13.

In Step 15, if the sheath tension is greater than the predetermined threshold value, the processing then goes to Step 16 in which the sheath pulling driving unit 21 is put off so that the sheath 6 is pulled, and locked and fixed in place (ST16), after which the control gets done.

With such sheath pulling mechanism 10 for the medical instrument 1 according to the fourth embodiment, it is possible to pull and fix the sheath 6 in place while measuring the sheath tension for precise correction of the slack in the sheath 6.

The sheath pulling mechanism 10 for the medical instrument 1 according to the fifth embodiment is now explained.

Figure 11A:
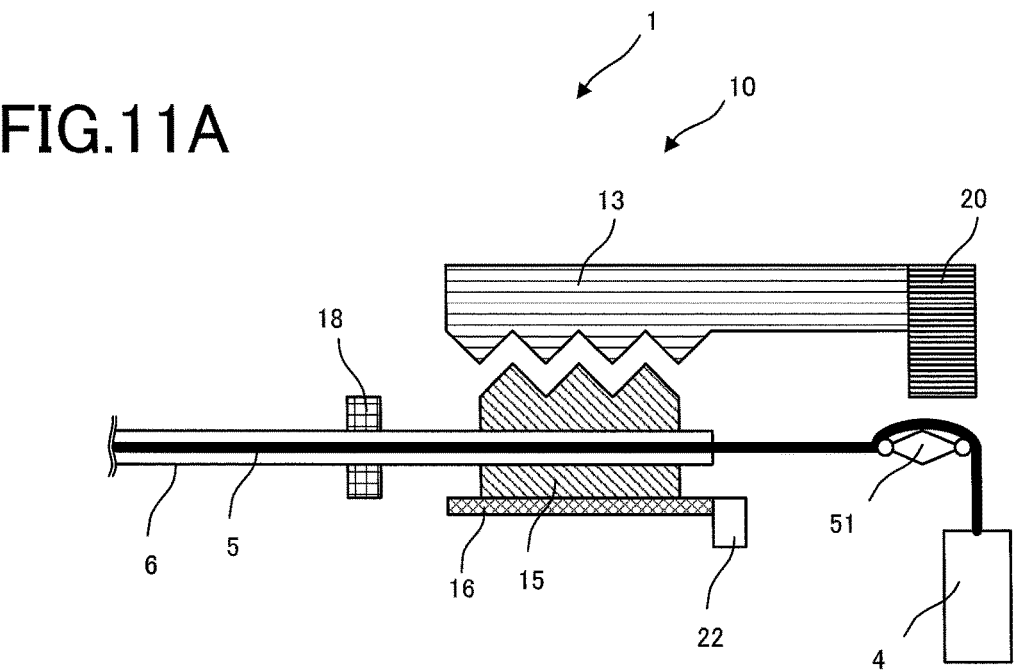
FIGS. 11A and 11B are a schematic view of the sheath pulling mechanism for the medical instrument according to the fifth embodiment.
Figure 11B:
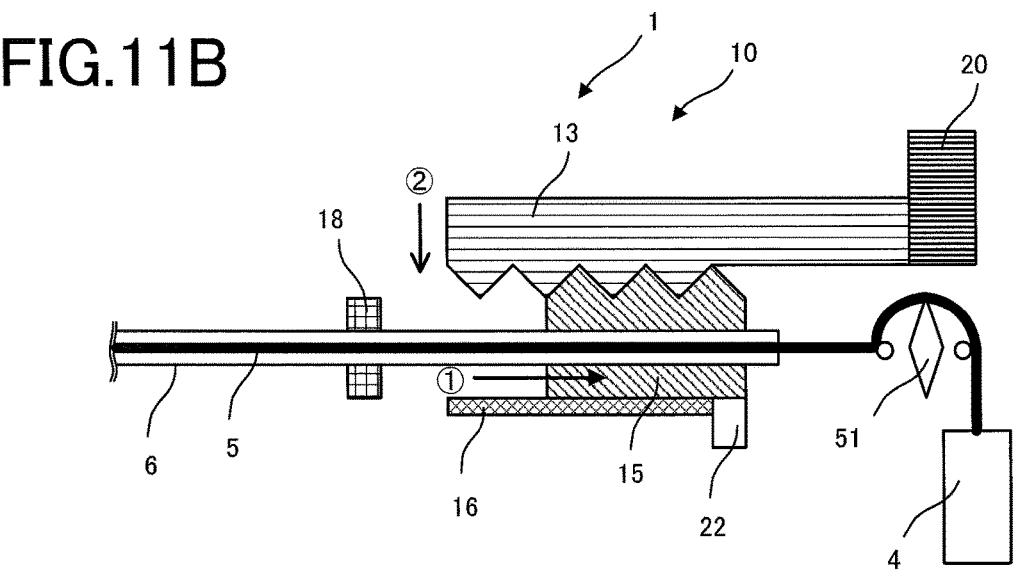

FIGS. 11A and 11B are is a schematic view of the sheath pulling mechanism 10 for the medical instrument 1 according to the fifth embodiment: FIG. 11A is a schematic view of the sheath pulling mechanism 10 according to the fifth embodiment before movement and FIG. 11B is a schematic view of the sheath pulling mechanism 10 according to the fifth embodiment after movement.

Instead of including the sheath pulling driving unit 21 for pulling the sheath 6 according to the third embodiment shown in FIGS. 6A and 6B, the sheath pulling mechanism 10 for the medical instrument 1 according to the fifth embodiment includes a wire path changing unit 51 for correcting a pulling path taken by the wire 5 for substantial pulling delivery of the wire 5, as shown in FIGS. 11A and 11B. The rest of the structure will not be explained anymore because of being similar to that of the sheath pulling mechanism 10 for the medical instrument 1 according to the third embodiment. In the fifth embodiment, the wire path changing unit 51 forms a pulling unit or a wire pulling unit, and the sheath lock driving unit 20 and sheath lock member 13 define together a sheath lock unit. Note here that the wire 5 may be pulled by the wire driving unit 4 without recourse to the wire path changing unit 51.

As shown in FIG. 11A, the sheath pulling mechanism 10 according to the fifth embodiment includes the wire path changing unit 51 that is capable of pulling the wire 5 to reduce the slack in the sheath 6. The sheath lock driving unit 20 is placed such that the sheath lock member 13 is movable in a direction of coming into mesh with, and going away from, the sheath support member 15. The sheath support member 15 is previously fixed to the sheath 6, and mounted on the sheath support member guide 16 in such a way as to be movable in a direction of pulling, and getting back, the sheath 6 as the sheath pulling driving unit 21 is driven.

The sheath pulling mechanism 10 is actuated as by a switch (not shown). First of all, the wire 5 is pulled by the wire path changing unit 51 to reduce the slack in the sheath 6. Subsequently, the sheath lock driving unit 20 is driven to bring the sheath lock member 13 into engagement with the sheath support member 15. Thus, the sheath 6 maintains shape in a slack-free state shown in FIG. 11B. Note here that whether or not the sheath 6 is locked may be determined by the actuation of the sheath lock driving unit 20 or, alternatively, whether or not the sheath pulling mechanism 10 is locked may be determined through detection of movement of the sheath lock member 13 as is the case with the lock detection unit 19 shown in FIGS. 4A and 4B.

With such sheath pulling mechanism 10 for the medical instrument 1 according to the fifth embodiment, the wire 5 can be pulled under a given force so that the sheath 6 can be pulled and fixed in a slack-free shape under a constant tension.

The sheath pulling mechanism 10 for the medical instrument 1 according to the sixth embodiment is now explained.

Figure 12:
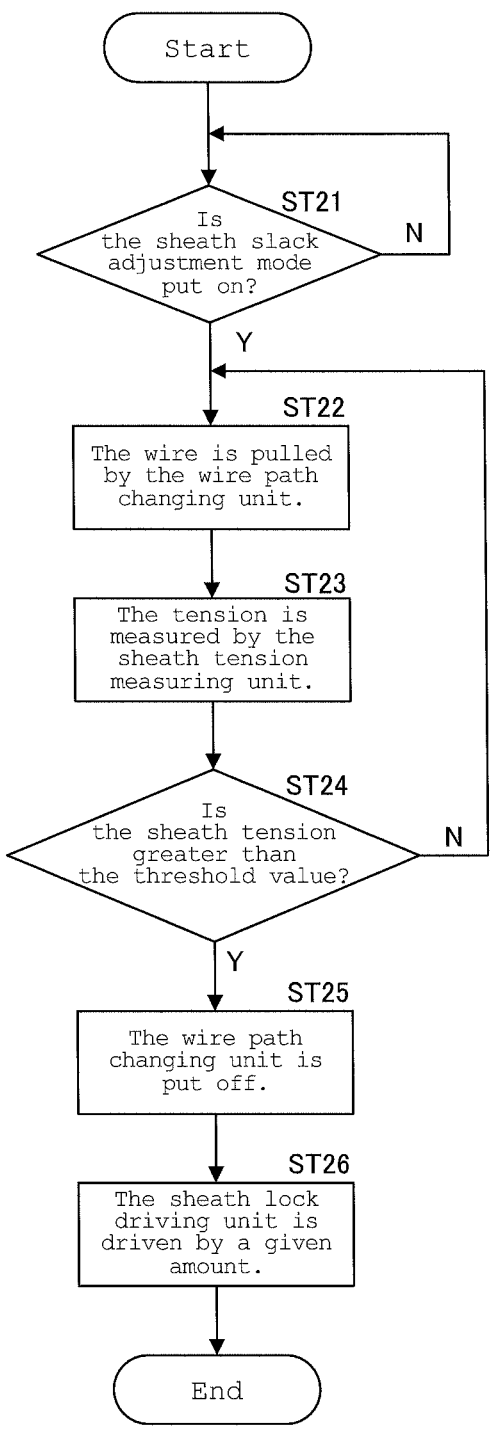
FIG. 12 is a control flowchart for the medical instrument according to the sixth embodiment.

FIG. 12 is a control flowchart for the medical instrument according to the sixth embodiment.

In the medical instrument 1 according to the sixth embodiment, the sheath tension measuring unit 22 is used to control the sheath pulling mechanism 10 for the medical instrument 1 according to the fifth embodiment shown in FIGS. 11A and 11B. As is the case with the third embodiment shown in FIGS. 6A and 6B, the sheath tension measuring unit 22 is preferably placed in the sheath support member guide 16, but it may be located in other position. In the sixth embodiment, the wire path changing unit 51 forms a pulling unit or a wire pulling unit, and the sheath lock driving unit 20 and sheath lock member 13 define together a sheath lock unit.

The medical instrument 1 according to the sixth embodiment includes the mode input unit 32 and sheath tension measuring unit 22 out of the input block 30 forming a part of the control block shown in FIG. 7. The mode input unit 32 detects that the sheath slack adjustment mode of reducing the slack in the sheath 6 is put on, and enters the resultant signal into the control unit 40. The tension of the sheath 6 is measured by the sheath tension measuring unit 22 to enter the resultant measurement into the control unit 40.

In the sixth embodiment, whether or not the sheath slack adjustment mode of the mode input unit 32 shown in FIG. 7 is put on is first determined in Step 21 (ST21), as shown in FIG. 12. In Step 21, if the sheath slack adjustment mode being put on is not detected, the processing then goes back to Step 21.

In Step 21, if the sheath slack adjustment mode being put on is detected, the processing then goes to Step 22 in which the wire path changing unit 51 is driven (ST22). Subsequently, the processing goes to Step 23 in which the sheath tension is measured by the sheath tension measuring unit 22 (ST23).

Then, the processing goes to Step 24 in which it is determined whether or not the sheath tension measured by the sheath tension measuring unit 22 is greater than a predetermined threshold value (ST24). In Step 24, if the sheath tension is not greater than the predetermined threshold value, the processing then goes back to Step 22.

In Step 24, if the sheath tension is greater than the predetermined threshold value, the processing then goes to Step 25 in which the wire path changing unit 51 is put off (ST25). Subsequently, the processing goes to Step 26 in which the sheath lock driving unit 20 is driven by a given amount to pull and fix the sheath 6 in place (ST26), after which the control gets done.

With such sheath pulling mechanism 10 for the medical instrument 1 according to the sixth embodiment, it is possible to pull and fix the wire 5 in place while measuring the sheath tension thereby making precise correction of the sheath 6 for the slack.

The sheath pulling mechanism 10 for the medical embodiment according to the seventh embodiment is now explained.

Figure 13:
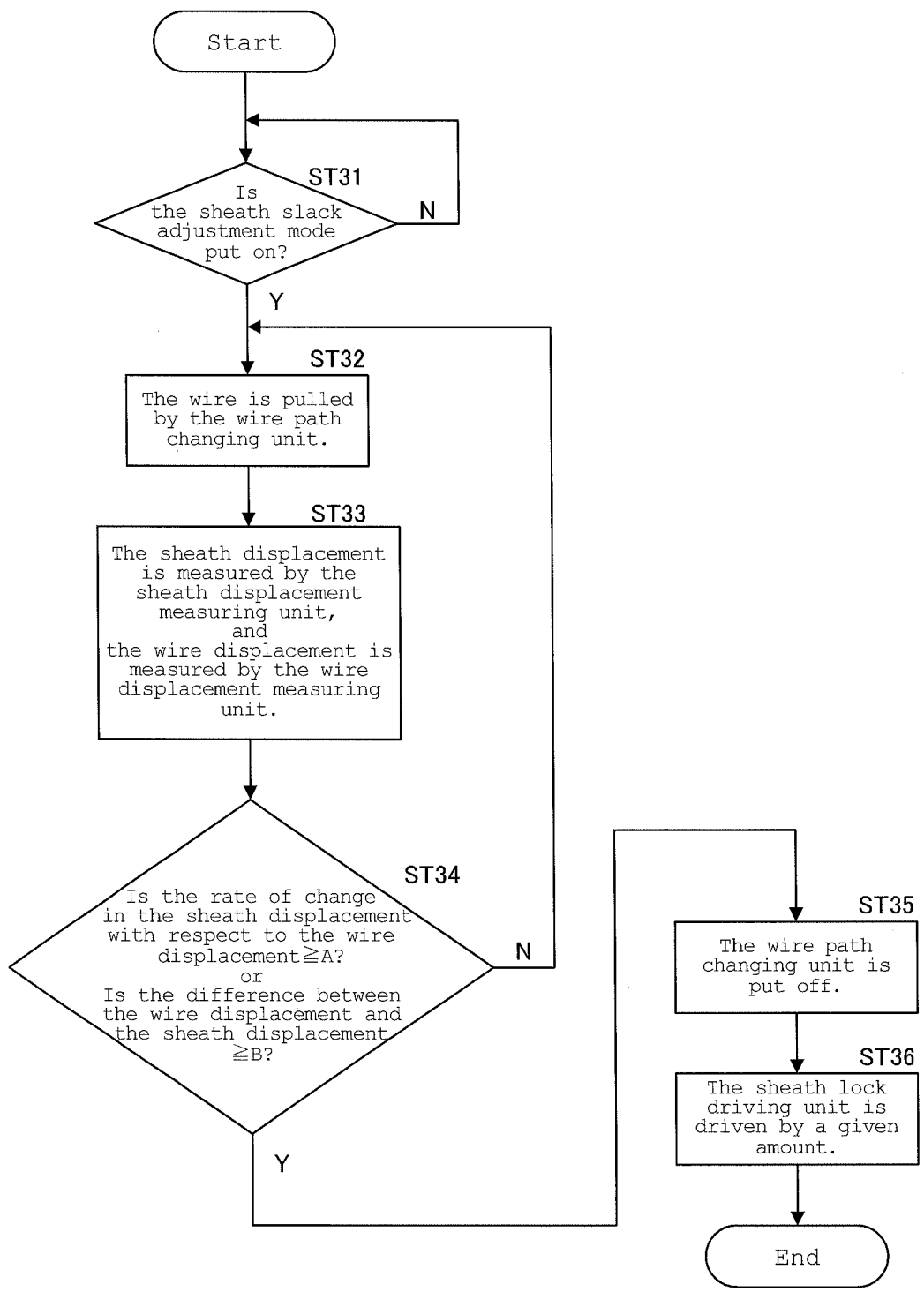
FIG. 13 is a control flowchart for the medical instrument according to the seventh embodiment.
Figure 14:
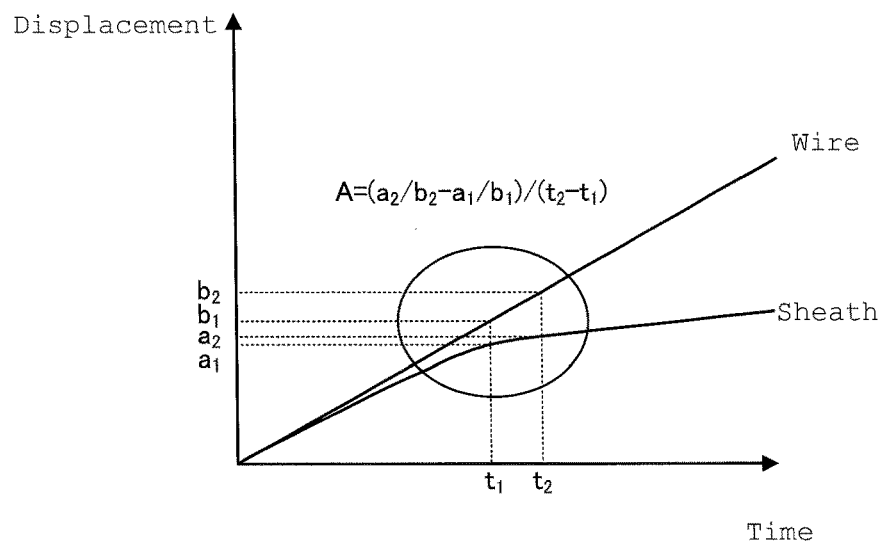
FIG. 14 is a wire displacement vs. sheath displacement diagram.
Figure 15:
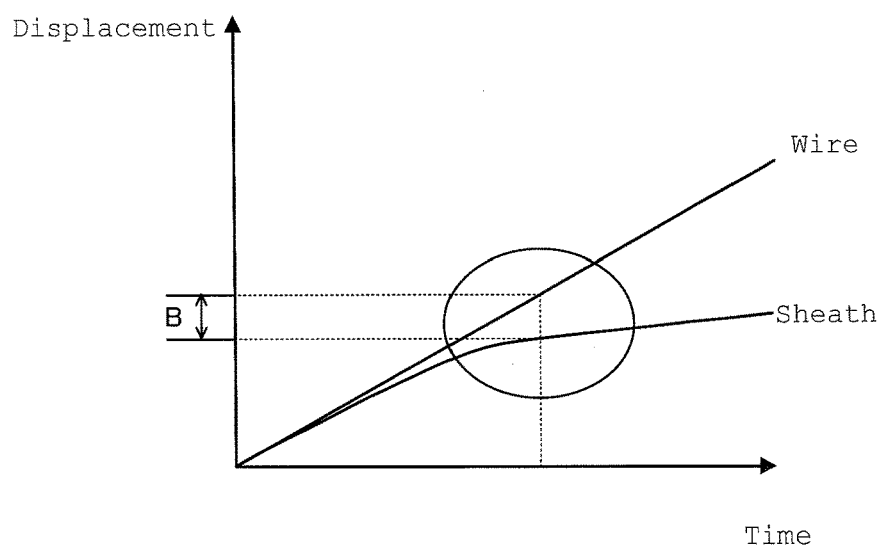
FIG. 15 is indicative of a difference in displacement between the wire and the sheath.

FIG. 13 is a control flowchart for the medical instrument according to the seventh embodiment, FIG. 14 is illustrative of a wire displacement vs. sheath displacement, and FIG. 15 is indicative of a difference in displacement between the wire and the sheath.

In the medical instrument 1 according to the seventh embodiment, the sheath displacement measuring unit 23 and wire displacement measuring unit 24 shown in FIG. 7 are used to control the sheath pulling mechanism 10 for the medical instrument 1 according to the fifth embodiment shown in FIGS. 11A and 11B. The sheath displacement measuring unit 23 and wire displacement measuring unit 24 may be located in any desired positions. In the seventh embodiment, the wire path changing unit 51 forms a sheath pulling unit and a wire pulling unit, and the sheath lock driving unit 20 and sheath lock member 13 define together a sheath lock unit.

The medical instrument 1 according to the seventh embodiment here includes the mode input unit 32, sheath displacement measuring unit 23 and wire displacement measuring unit 24 out of the input block 30 forming a part of the control block shown in FIG. 7. The mode input unit 32 detects that the sheath slack adjustment mode of reducing the slack in the sheath 6 is put on, and enters the resultant signal into the control unit 40. The sheath displacement measuring unit 23 measures a displacement of the sheath 6 and enters the resultant signal into the control unit 40, and the wire displacement measuring unit 24 measures a displacement of the wire 5 and enters the resulting signal into the control unit 40.

In the seventh embodiment, whether or not the sheath slack adjustment mode of the mode input unit 32 shown in FIGS. 6A and 6B is put on is first determined in Step 31, as shown in FIG. 13 (ST31). In Step 31, if the sheath slack adjustment mode being put on is not detected, the processing then goes back to Step 31.

In Step 31, if the sheath slack adjustment mode being put on is detected, the processing then goes to Step 32 in which the wire path changing unit 51 is driven (ST32). Subsequently, the processing goes to Step 33 in which the sheath displacement measuring unit 23 is allowed to measure the displacement of the sheath 6 and the wire displacement measuring unit 24 is allowed to measure the displacement of the wire 5 (ST33).

Then, the processing goes to Step 34 in which it is determined whether or not the rate of change of displacement of the sheath 6, as measured by the sheath displacement measuring unit 23, with respect to the displacement of the wire 5 as measured by the wire displacement measuring unit 24 is greater than a predetermined value A (ST34).

In Step 34, if the rate of change of displacement of the sheath 6 with respect to the displacement of the wire 5 is not greater than the predetermined value A, the processing then goes to Step 32.

In Step 34, if the rate of change of displacement of the sheath 6 with respect to the displacement of the wire 5 is greater than the predetermined value A, the processing then goes to Step 35 in which the wire path changing unit 51 is put off (ST35). Subsequently, the processing goes to Step 36 in which the sheath lock driving unit 20 is driven by a given amount so that the sheath 6 is pulled and locked in place (ST36), after which the control gets done.

It is here to be noted that in place of the rate of change of displacement of the wire 5 and sheath 6, it may be determined in Step 34 whether or not a difference between the displacement of the wire 5 as measured by the wire displacement measuring unit 24 and the displacement of the sheath 6 as measured by the sheath displacement measuring unit 23 is greater than a predetermined value B. In Step 34, if the displacement difference between the wire 5 and the sheath 6 is not greater than the predetermined value B, the processing then goes back to Step 32, and if that displacement difference is greater than the predetermined value B, the processing then goes to Step 35.

With such sheath pulling mechanism 10 for the medical instrument 1 according to the seventh embodiment, the wire 5 can be pulled and fixed in place while measuring the displacements of the sheath 6 and wire 5, so that the slack in the sheath 6 can be corrected with precision.

The sheath pulling mechanism 10 for the medical instrument 1 according to the eighth embodiment is now explained.

Figure 16:
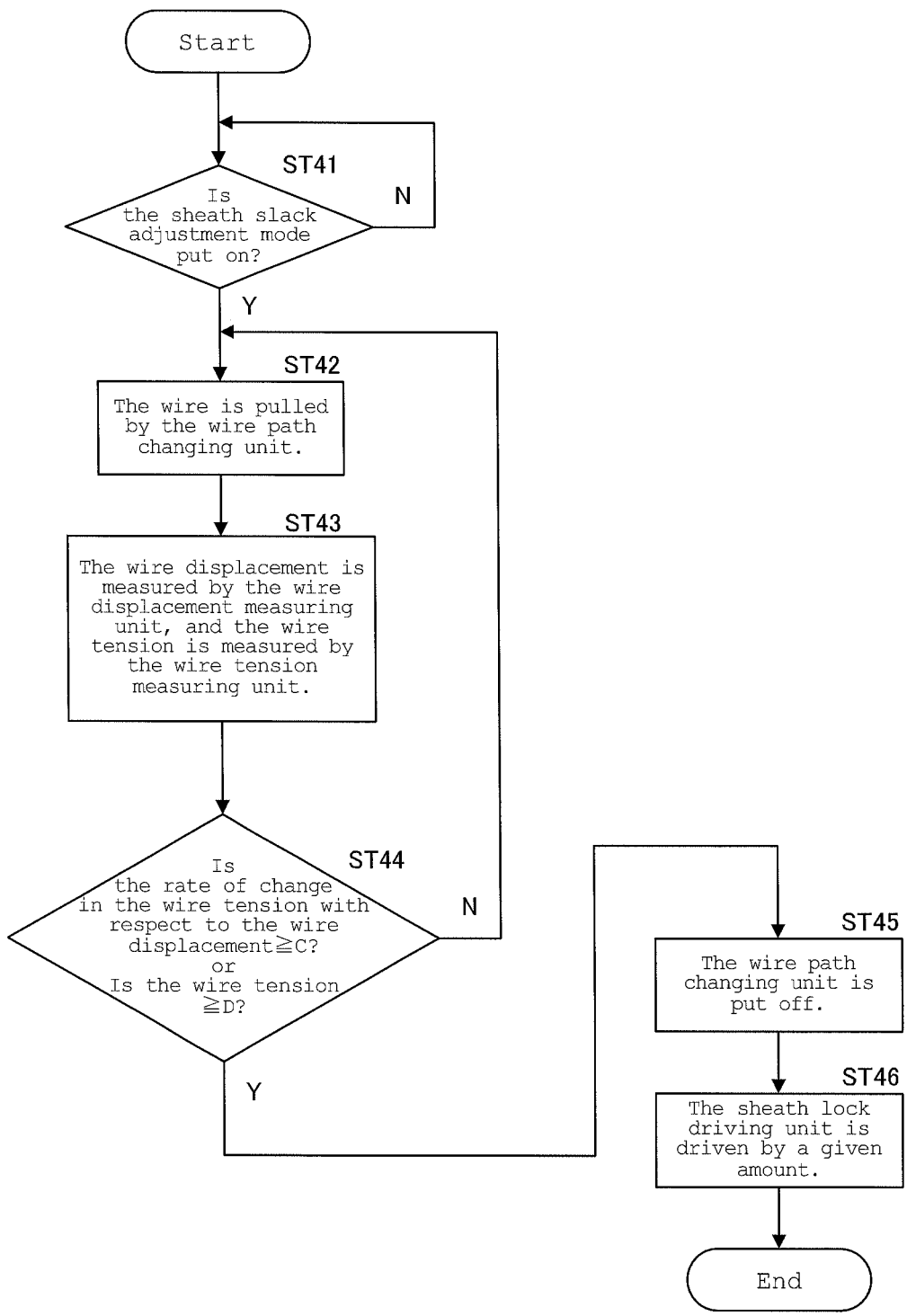
FIG. 16 is a control flowchart for the medical instrument according to the eighth embodiment.
Figure 17:
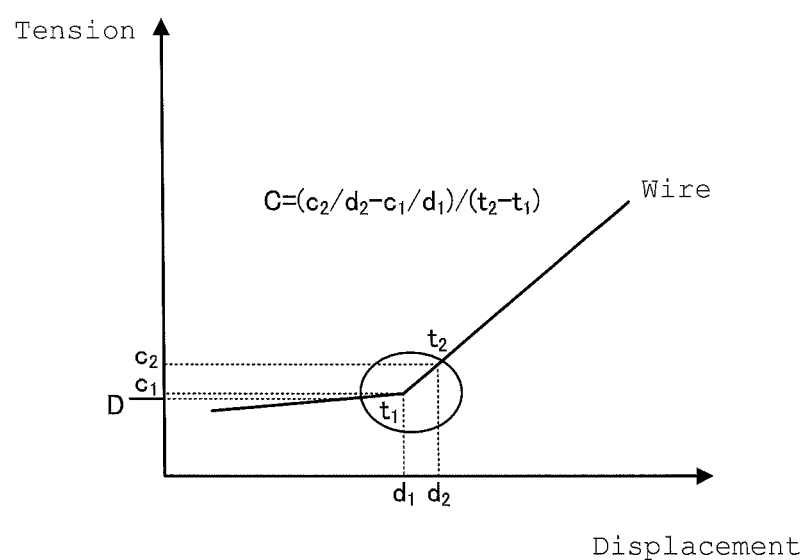
FIG. 17 is a wire displacement vs. wire tension diagram.

FIG. 16 is a control flowchart for the medical instrument 1 according to the eighth embodiment, and FIG. 17 is indicative of a wire displacement vs. wire tension.

In the medical instrument 1 according to the eighth embodiment, the wire displacement measuring unit 24 and wire tension measuring unit 25 are used to control the sheath pulling mechanism 10 for the medical instrument 1 according to the fifth embodiment shown in FIGS. 11A and 11B. The wire displacement measuring unit 24 and wire tension measuring unit 25 may be located in any desired positions. In the eighth embodiment, the wire path changing unit 51 forms a sheath pulling unit and a wire pulling unit, and the sheath lock driving unit 20 and sheath lock member 13 define together a sheath lock unit.

The medical instrument 1 according to the eighth embodiment here includes the mode input unit 32, wire displacement measuring unit 24 and wire tension measuring unit 25 out of the input block 30 forming a part of the control block shown in FIG. 7. The mode input unit 32 detects that the sheath slack adjustment mode of reducing the slack in the sheath 6 is put on, and enters the resultant signal into the control unit 40. The wire displacement measuring unit 24 measures a displacement of the wire 5 and enters the resultant signal into the control unit 40, and the wire tension measuring unit 25 measures the tension of the wire 5 and enters the resulting signal into the control unit 40.

In the eighth embodiment, whether or not the sheath slack adjustment mode of the mode input unit 32 shown in FIG. 7 is put on is first determined in Step 41, as shown in FIG. 16 (ST41). In Step 42, if the sheath slack adjustment mode being put on is not detected, the processing goes back to Step 42.

In Step 41, if the sheath slack adjustment mode being put on is detected, the processing then goes to Step 42 in which the wire path changing unit 51 is driven (ST42). Subsequently, the processing goes to Step 43 in which the sheath displacement measuring unit 24 is allowed to measure the displacement of the wire 5 and the wire tension measuring unit 25 is allowed to measure the tension of the wire 5 (ST43).

Then, the processing goes to Step 44 in which it is determined whether or not the rate of change of tension of the wire 5, as measured by the wire tension measuring unit 25, with respect to the displacement of the wire 5 as measured by the wire displacement measuring unit 24 shown in FIG. 17 is greater than a predetermined value C (ST44).

In Step 44, if the rate of change of tension of the wire 5 with respect to the displacement of the wire 5 is not greater than the predetermined value C, the processing then goes back to Step 42.

In Step 44, if the rate of change of tension of the wire 5 with respect to the displacement of the wire 5 is greater than the predetermined value C, the processing then goes to Step 45 in which the wire path changing unit 51 is put off (ST45). Subsequently, the processing goes to Step 46 in which the sheath lock driving unit 20 is driven by a given amount so that the sheath 6 is pulled and locked in place (ST46), after which the control gets done.

It is here to be noted that in place of the rate of change of tension of the wire 5 with respect to the displacement of the wire 5, it may be determined in Step 44 whether or not the tension of the wire 5 as measured by the wire tension measuring unit 25 is greater than a predetermined value D. In Step 44, if the tension of the wire 5 is not greater than the predetermined value D, the processing goes back to Step 42, and if the tension of the wire 5 is greater than the predetermined value D, the processing goes to Step 45.

With such sheath pulling mechanism 10 for the medical instrument 1 according to the eighth embodiment, the wire 5 can be pulled and fixed in place while measuring the displacements of the sheath 6 and wire 5, so that the slack in the sheath 6 can be corrected with precision.

The structure of coupling the insert unit 2 to the wire driving unit 4 shown in FIG. 1 or 2 is now explained. Note here that in what follows, a stopper 60 defines the sheath lock unit.

Figure 18A:
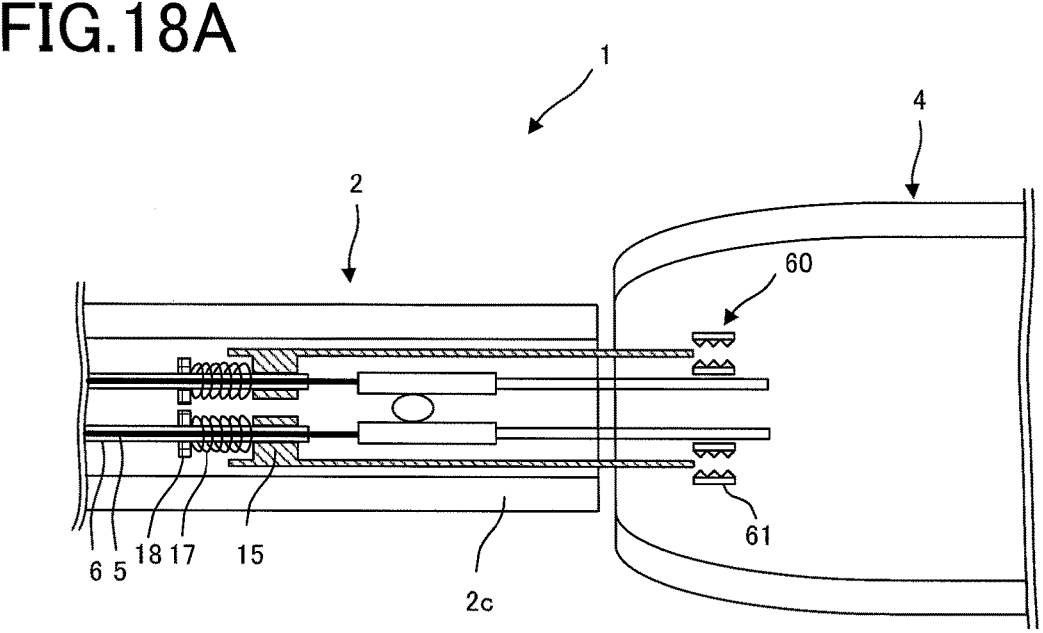
FIGS. 18A and 18B are illustrative of the first example of the structure of coupling the insert unit to the wire driving unit in the medical instrument according to one embodiment.
Figure 18B:
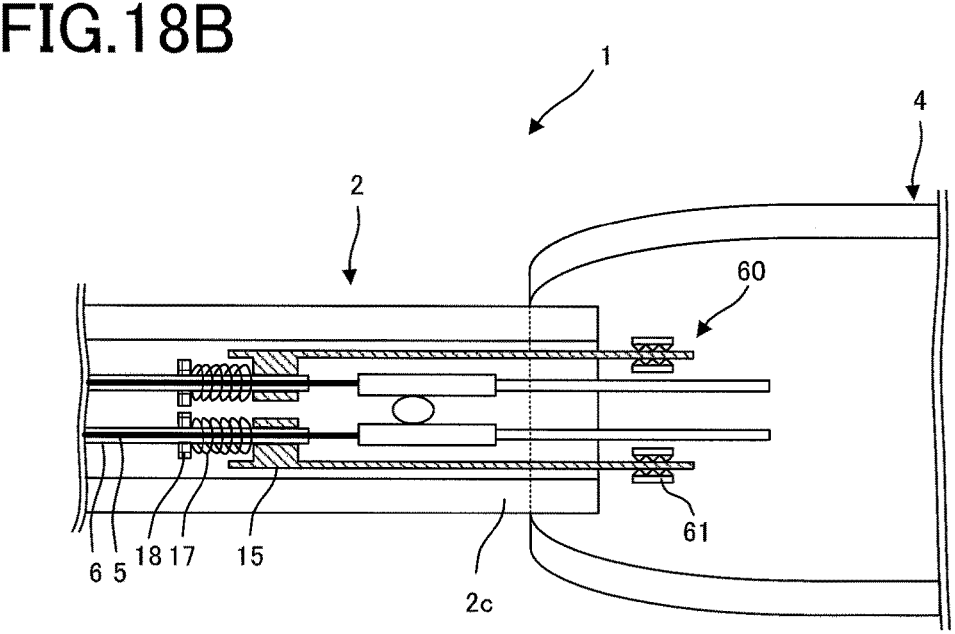

FIGS. 18A and 18B are illustrative of a first example of the structure of coupling the insert unit 2 to the wire driving unit 4 for the medical instrument 1 according to the embodiment described herein: FIG. 18A shows an example wherein the insert unit 2 is not yet coupled to the wire driving unit 4, and FIG. 18B shows an example wherein the insert unit 2 is coupled to the wire driving unit 4.

To couple the insert unit 2 to the wire driving unit 4, the flexible portion 2c of the insert unit 2 is inserted from the state of FIG. 18A into the wire driving unit 4, as shown in FIG. 18B. At this time the sheath support member 15 is locked by the stopper 60 on the operating unit 3 side. The stopper 60 should preferably be put into actuation at the same time as the insert unit 2 is mounted on the wire driving unit 4. Note here that the stopper 60 may be actuated by a switch after the attachment of the insert unit 2 to the wire driving unit 4. The stopper 60 should also be preferably designed to be released as by a release switch (not shown).

In the first example shown in FIGS. 18A and 18B, clips 61 are used as the stopper 60. Upon insertion of the insert unit 2 into the wire driving unit 4, the clips 61 hold down the sheath support member 15. Note here that instead of using the clips 61, a magnet and such may be used, and that the clips are preferably designed to be set free as by a switch (not shown).

Figure 19A:
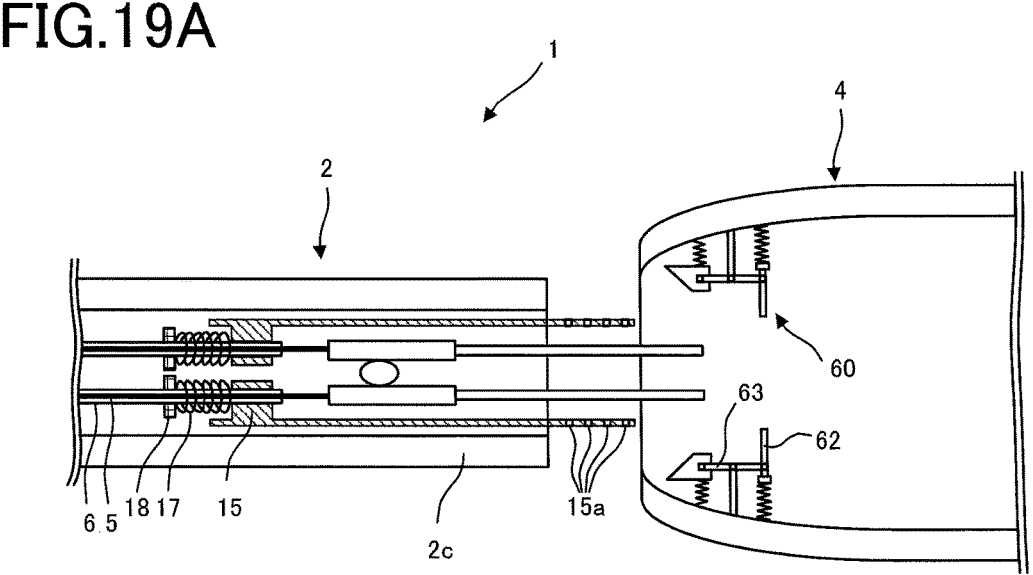
FIGS. 19A and 19B are is illustrative of the second example of the structure of coupling the insert unit to the wire driving unit in the medical instrument according to the embodiment.
Figure 19B:
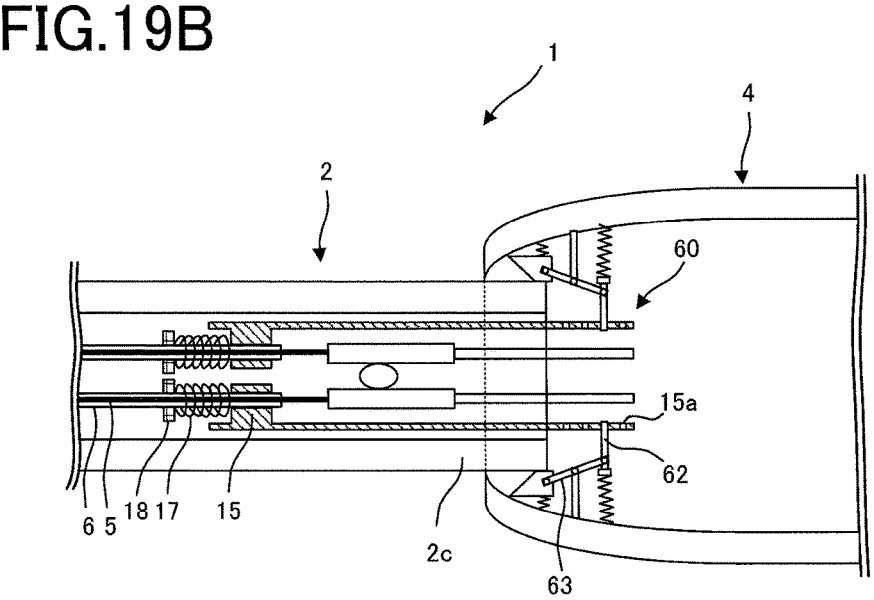

FIGS. 19A and 19B are illustrative of a second example of the structure of coupling the insert unit 2 to the wire driving unit 4 in the medical instrument 1 according to the embodiment described herein: FIG. 19A shows an example wherein the insert unit 2 is not yet coupled to the wire driving unit 4, and FIG. 19B shows an example wherein the insert unit 2 is coupled to the wire driving unit 4.

In the second example of FIGS. 19A and 19B, a pin 62 is used as the stopper 60, and upon insertion of the insert unit 2 into the driving unit 4, a linkage mechanism 63 is actuated to insert the pin 62 into an opening 15a formed in the sheath support member 15. In the second example, the pin 62 defines the sheath lock member. The pin 62 is preferably capable of deinsertion out of the opening 15a as by a release switch (not shown).

Figure 20A:
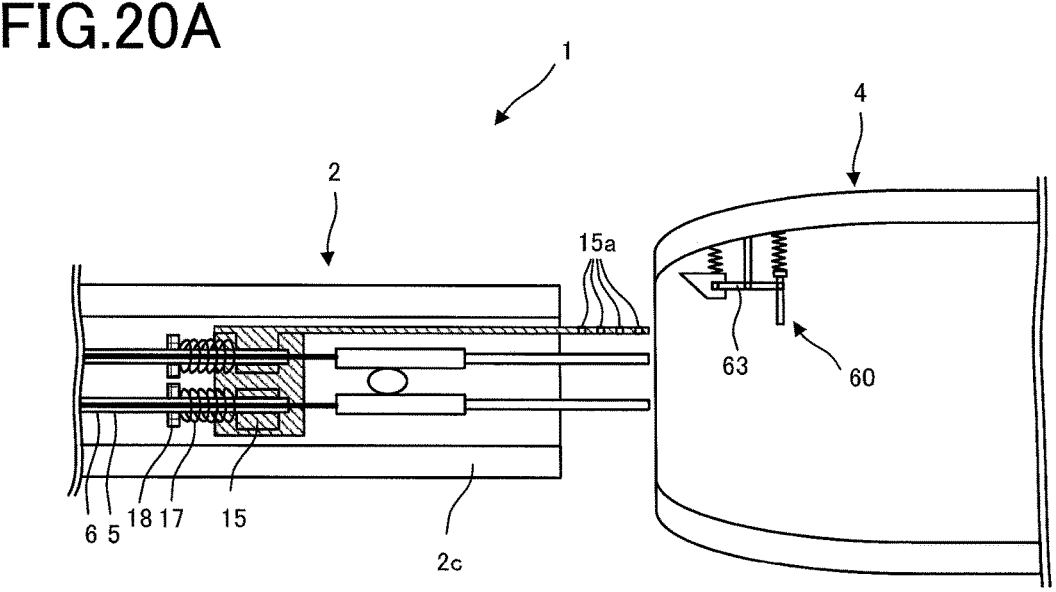
FIGS. 20A and 20B are illustrative of the third example of the structure of coupling the insert unit to the wire driving unit in the medical instrument according to one embodiment.
Figure 20B:
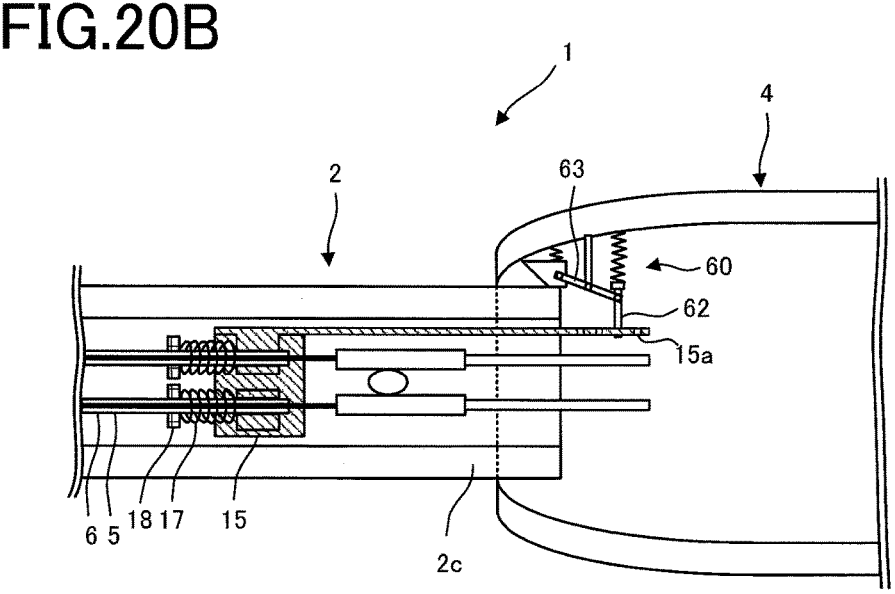

FIGS. 20A and 20B are illustrative of a third example of the structure of coupling the insert unit 2 to the wire driving unit 4 in the medical instrument 1 according to the embodiment described herein: FIG. 20A shows an example wherein the insert unit 2 is not yet coupled to the wire driving unit 4, and FIG. 20B shows an example wherein the insert unit 2 is coupled to the wire driving 4.

In the third example of FIGS. 20A and 20B, a pin 62 is used as the stopper 60, as is the case with the second example. However, it is noted that two sheaths 6 are supported by the sheath support member 15. Upon insertion of the insert unit 2 into the wire driving unit 4, a linkage mechanism 63 at one site is actuated to insert the pin 62 in an opening 15a formed in the sheath support member 15. In the third example, the pin 62 defines the sheath lock member. The pin 62 is preferably capable of being taken out of the opening 15a as by a release switch (not shown).

Figure 21A:
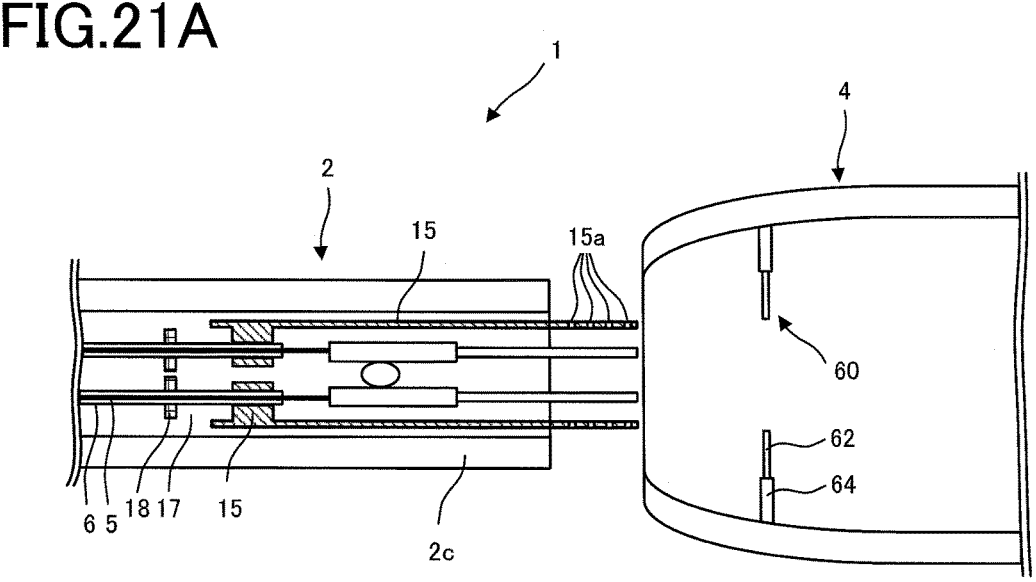
FIGS. 21A and 21B are illustrative of the fourth example of the structure of coupling the insert unit to the wire driving unit in the medical instrument according to one embodiment.
Figure 21B:
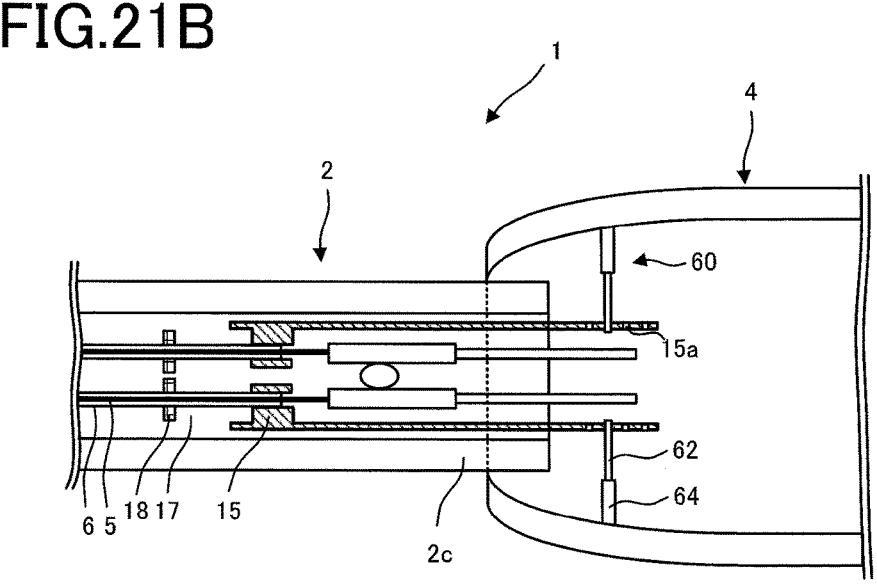

FIGS. 21A and 21B are illustrative of a fourth example of the structure of coupling the insert unit 2 to the wire driving unit 4 in the medical instrument 1 according to the embodiment described herein: FIG. 21A shows an example wherein the insert unit 2 is not yet coupled to the wire driving unit 4, and FIG. 21B shows an example wherein the insert unit 2 is coupled to the wire driving unit 4.

In the fourth example of FIGS. 21A and 21B, a pin 62 is used as the stopper 60, as is the case with the second example. However, the pin 62 has a structure of being actuated by an actuator 64. As the actuator 64 is put by a switch into operation after insertion of the insert unit 2 into the driving unit 4, it permits for insertion of the pin 62 into an opening 15a formed in the sheath support member 15. In the fourth example, the pin 62 defines the sheath lock member. The actuator 64 is preferably put in opposite operation to take the pin 62 out of the opening 15a.

A surgical system 90 is now explained as one example of the medical system to which the medical instrument 1 according to the embodiment described herein is applied.

Figure 22:
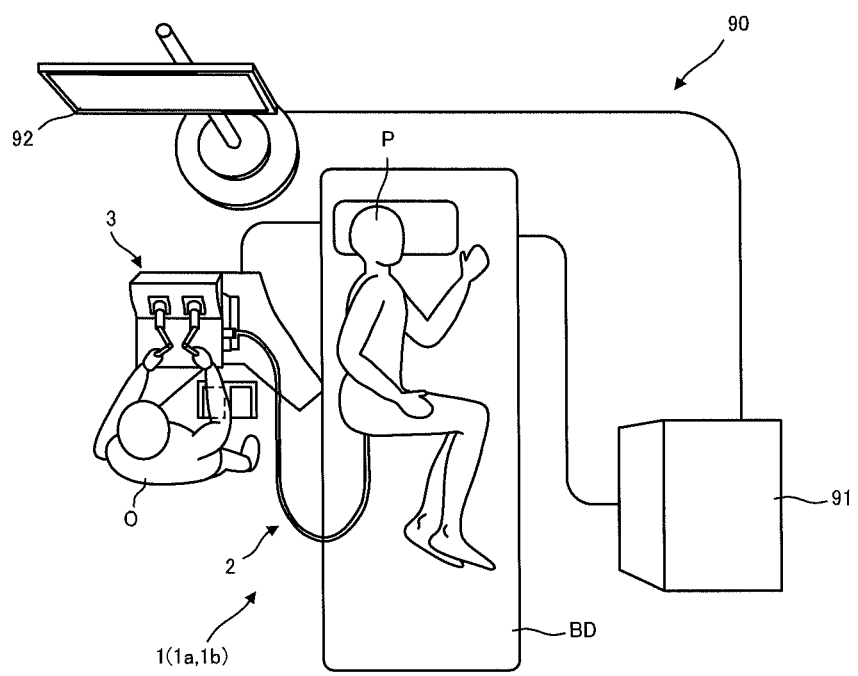
FIG. 22 is illustrative of the surgical system to which the medical instrument according to one embodiment is applied.
Figure 23:
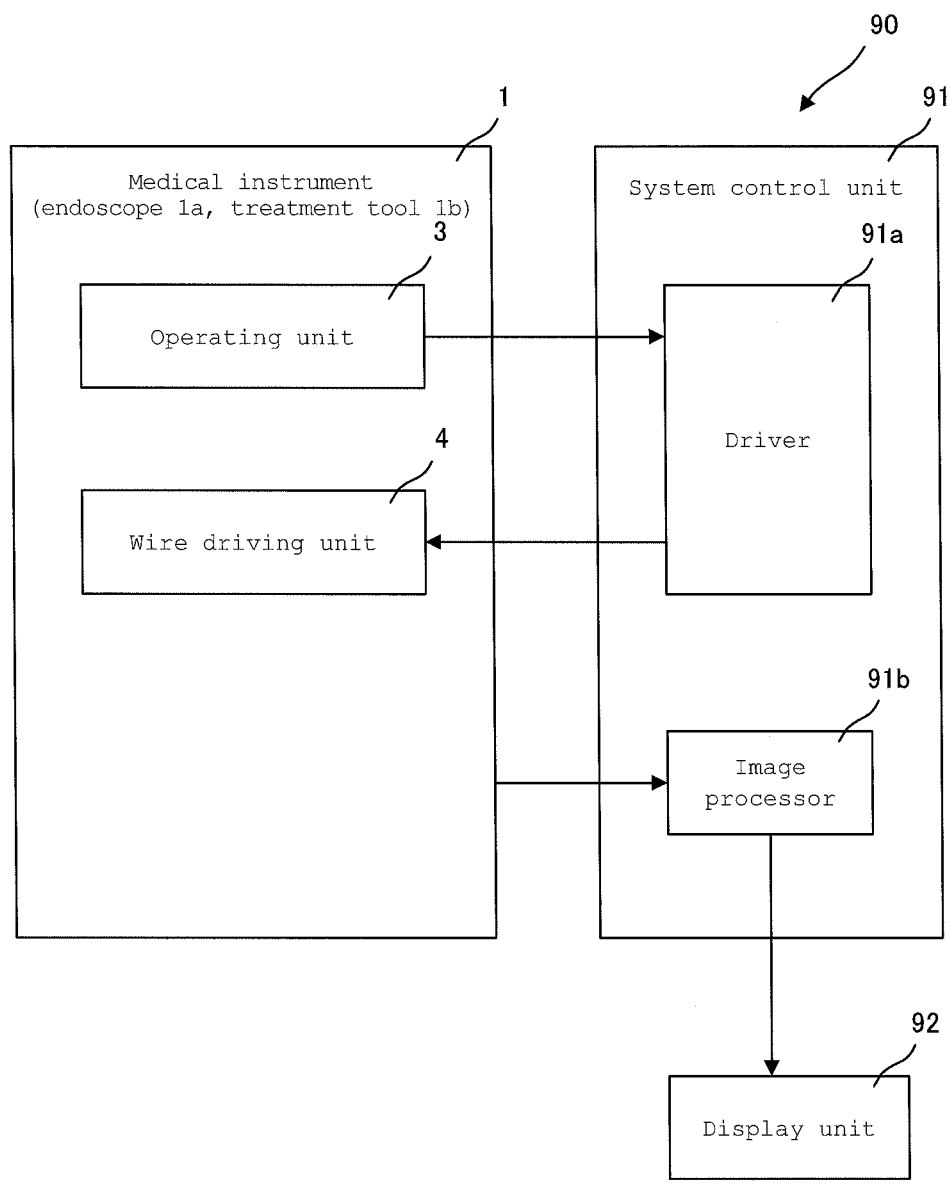
FIG. 23 is illustrative in system architecture of the surgical system to which the medical instrument according to one embodiment is applied.

FIG. 22 is illustrative of a surgical system 90 to which the medical instrument 1 according to the embodiment described herein is applied, and FIG. 23 is illustrative in system architecture of the surgical system 90 to which the medical instrument 1 according to the embodiment described herein is applied.

The medical instrument 1 is applied to the surgical system 90 according to the embodiment described herein. The surgical system 90 includes an operating unit 3 operated by an operator O, a medical instrument 1 such as an endoscope 1a having a distal-end insert unit 2 capable of being inserted into the interior of the body of a patient P lying down on an operating table BD, for instance, a soft organ like the large intestine, a system control unit 91 for controlling the medical instrument 1, and a display unit 92 for displaying an image acquired through the medical instrument 1.

The operating unit 3 includes a pair of operating handles attached to an operating table, and a footswitch or the like placed on the floor surface. The operating unit 3 may have a multi-joint structure. The angle of the operating unit 3 in operation is acquired by an angle acquisition unit such as an encoder and in response to the resultant signal, the system control unit 91 puts the wire driving unit 4 into operation by way of a driver 91a.

The image acquired as by the endoscope 1a is sent out to an image processor 91b within the system control unit 91, and the image processed by the image processor 91b is displayed on the display unit 92. Then, the operator O operates the medical instrument 1 while viewing the image appearing on the display unit 92.

According to such surgical system 90, it is possible to display unerring images asked for by the operator O thereby putting the medical instrument 1 into more unerring operation.

It is here noted that the medical instrument 1 used with the surgical system 90 may be the endoscope 1a used in the first embodiment, the treatment tool 1b inserted through the endoscope 1a as in the second embodiment, or a treatment tool 1b separate from the endoscope 1a.

As described above, the medical instrument 1 according to one embodiment includes a wire 5, a flexible sheath 6 through which the wire 5 is inserted, a wire driving unit 4 for driving the wire 5, a passive unit 2 that is put into operation as the wire is driven, a sheath pulling unit 14, 17, 21, 51, for pulling the sheath 6, and a sheath lock unit 12, 13, 20 for locking movement of the sheath 6. It is thus possible to reduce the slack in the sheath 6 unerringly in association with a change in the shape of the passive unit 2.

The medical instrument 1 according to one embodiment includes a sheath lock driving unit 20 for moving a sheath lock member 13 in such a way as to lock a sheath support member 15 in place. It is thus possible to hold the sheath lock member 13 unerringly.

In the medical instrument 1 according to one embodiment, the sheath pulling unit 17 includes a biasing member 17 for biasing the sheath support member 15 to pull the sheath 6. It is thus possible to reduce the slack in the sheath 6 through a simplified construction.

In the medical instrument 1 according to one embodiment, the sheath pulling unit 17 includes a sheath pulling driving unit 21 for driving the sheath support member 15 to pull the sheath 6. It is thus possible to reduce the slack in the sheath 6 rapidly and unerringly.

The medical instrument 1 according to one embodiment includes a control unit 40 for controlling the sheath pulling driving unit 21 and sheath lock driving unit 20 depending on a specific state of the sheath 6. It is thus possible to reduce the slack in the sheath 6 unerringly depending on a specific situation.

The medical instrument 1 according to one embodiment includes a sheath tension measuring unit 22 for measuring the tension of the sheath 6 wherein when a measurement obtained by the sheath tension measuring unit 22 is greater than a predetermined threshold value, the control unit 40 drives the sheath lock driving unit 20 to lock the sheath support member 15 in place. It is thus possible to reduce the slack in the sheath 6 unerringly depending on a specific situation.

In the medical instrument 1 according to one embodiment, the control unit 40 drives the sheath pulling driving unit 21, and puts off the sheath pulling driving unit 21 depending on a measurement obtained by the sheath tension measuring unit 22 and drives the sheath lock driving unit 20 to lock the sheath support member 15 in place. It is thus possible to reduce the slack in the sheath 6 more unerringly.

In the medical instrument 1 according to one embodiment, the control unit 40 drives the sheath lock driving unit 20 to lock the sheath support member 15 in place, after which the control unit 40 drives the sheath pulling driving unit 21 and puts off the sheath pulling driving unit 21 depending on a measurement obtained by the sheath tension measuring unit 22. It is thus possible to reduce the slack in the sheath 6 more unerringly.

The medical instrument 1 according to one embodiment includes a sheath pulling unit 14, 51 capable of pulling the wire 5 and pulling the sheath 6 by the thus pulled wire 5. It is also possible to reduce the slack in the sheath 6 by pulling the wire 5.

In the medical instrument 1 according to one embodiment, the wire pulling unit 51 includes a wire path changing unit 51 for changing a path taken by the wire 5 coupled to and pulled by the wire driving unit 4. It is thus possible to reduce the slack in the sheath 6 through a simplified construction.

The medical instrument 1 according to one embodiment includes a sheath tension measuring unit 22 for measuring the tension of the sheath 6 wherein the control unit 40 drives the sheath lock driving unit 20 when a measurement obtained by the sheath tension measuring unit 22 is greater than a predetermined threshold value. It is thus possible to reduce the slack in the sheath 6 unerringly depending on a specific situation.

The medical instrument 1 according to one embodiment includes a sheath displacement measuring unit 23 for measuring the displacement of the sheath 6 and a wire displacement measuring unit 24 for measuring the displacement of the wire 5, wherein the control unit 40 drives the sheath lock driving unit 20 depending on the rate of change in the sheath displacement, as measured by the sheath displacement measuring unit 23, with respect to the displacement of the wire as measured by the wire displacement measuring unit 24. It is thus possible to reduce the slack in the sheath 6 unerringly depending on a specific situation.

The medical instrument 1 according to one embodiment includes a sheath displacement measuring unit 23 for measuring the displacement of the sheath 6 and a wire displacement measuring unit 24 for measuring the displacement of the wire 5, wherein the control unit 40 drives the sheath lock driving unit 20 depending on a difference between the wire displacement as measured by the wire displacement measuring unit 24 and the sheath displacement as measured by the sheath displacement measuring unit 23. It is thus possible to reduce the slack in the sheath 6 unerringly depending on a specific situation.

There is a wire tension measuring unit 25 provided for measuring the tension of the wire 5, and the control unit 40 drives the sheath lock driving unit 20 when a measurement obtained by the wire tension measuring unit 25 is greater than a predetermined threshold value. It is thus possible to reduce the slack in the sheath 6 unerringly depending on a specific situation.

The medical instrument 1 according to one embodiment includes a wire displacement measuring unit 24 for measuring the displacement of the wire 5 and a wire tension measuring unit 25 for measuring the tension of the wire 5, wherein the control unit 40 drives the sheath lock driving unit 20 depending on the rate of change in the wire tension, as measured by the wire tension measuring unit 25, with respect to the wire displacement as measured by the wire displacement measuring unit 24. It is thus possible to reduce the slack in the sheath 6 unerringly depending on a specific situation.

In the medical instrument 1 according to one embodiment, the insert unit 2 and the wire driving unit 4 are detachable from each other, and upon attachment of the insert unit 2 to the wire driving unit 4, the sheath lock member 13 locks the sheath support member 15 in place. It is thus possible to achieve rapid locking.

In the medical system 90 according to one embodiment, the medical instrument 1 is an endoscope 1a including a viewing optical system, an imaging device and a lighting optical system, and a passive unit 2 is defined by a distal-end portion 2a of the endoscope 1a to which one end of a wire 5 is attached and a flexible portion 2c through which the wire 5 and sheath 6 are inserted. The medical system 90 further includes an operating unit 3 for driving a wire driving unit 4, to which the other end of the wire 5 is attached, to put the distal-end portion 2a and flexible portion 2c into operation, a display unit 92 for displaying an image acquired through the endoscope 1a, and a system control unit 91 for putting the operating unit 3 into operation thereby controlling the endoscope 1a and permitting the image acquired through the endoscope 1a to be displayed on the display unit 92. It is thus possible to reduce the slack in the sheath 6 unerringly in association with a change in the shape of the flexible portion 2c thereby applying unerring treatments and producing unerring screen displays depending on a specific situation.

In the medical system 90 according to one embodiment, the medical instrument 1 is defined by a treatment tool 1b for applying treatments to an affected site (of interest), and the passive unit 2 is defined by a distal end portion 2a of the treatment tool 1b to which one end of a wire 5 is attached and a flexible portion 2c through which the wire 5 and sheath 6 are inserted. The medical system 90 further includes an operating unit 3 for driving a wire driving unit 4, to which the other end of the wire 5 is attached, to put the distal end portion 2a and flexible portion 2c into operation, an endoscope 1a including a viewing optical system, an imaging device and a lighting optical system, a display unit 92 for displaying an image acquired through the endoscope 1a, and a system control unit 91 for controlling the treatment tool 1b by operation of the operating unit 3 and permitting the image acquired through the endoscope 1a to be displayed on the display unit 92. It is thus possible to reduce the slack in the sheath 6 unerringly in association with a change in the shape of the flexible portion 2c, thereby applying unerring treatments or producing unerring screen displays depending on specific situation. It is also possible to display endoscopic images and statuses of the treatment tool at the same time thereby improving on the operability of the medical instrument 1.

In the medical system 90 according to one embodiment, the treatment tool 1b is inserted through the endoscope 1a. It is thus possible to produce screen displays of the affected site on the eye level of the treatment tool thereby improving on the operability of the medical instrument 1.

While the embodiments as described above have been explained with the use of the sheath support member 15, it is to be understood that the sheath 6 may be provided with steps or ramps to support the sheath 6 or just only friction may be used to support the sheath 6, dispensing with the sheath support member 15. The wire 5 may be formed of a wire member such as a single wire, a stranded wire, a knitted wire, and so on.

It is here to be appreciated that the invention is in no sense limited to such embodiments as described above. While the explanation of some embodiments embraces numerous specific details for illustration, it would be obvious to those skilled in the art that diverse variations or modifications made thereto are included within the scope of the invention. In other words, illustrative embodiments of the invention are described without excluding generality from the claimed inventions and imposing any limitation thereon.

REFERENCE SIGNS LIST

1: Medical instrument
2: Insert unit (passive unit)

2a: Distal-end portion (passive portion)
2b: Curving portion (passive portion)
2c: Flexible portion (passive portion)
3: Operating unit
4: Wire driving unit
5: Wire
6: Sheath
7: Outer cover
10: Sheath lock mechanism
11: Case
12: Sheath lock-operation unit (sheath lock unit)
13: Sheath lock member (sheath lock unit)
15: Sheath support member (sheath pulling unit)
16: Sheath support member guide
18: Through-the-sheath unit
20: Sheath lock driving unit (sheath lock unit)
21: Sheath pulling driving unit (sheath pulling unit)
30: Input block
32: Mode input unit
22: Sheath tension measuring unit
23: Sheath displacement measuring unit
24: Wire displacement measuring unit
25: Wire tension measuring unit
40: Control unit
50: Output block
51: Wire path changing unit (pulling unit, wire pulling unit)
60: Stopper (sheath lock unit)
61: Clips (sheath lock unit)
62: Pin (sheath lock unit)
90: Medical system

The invention claimed is:

1. A medical instrument comprising:
a wire;
a flexible sheath through which the wire is inserted;
a wire driving unit for driving the wire;
a passive unit that is put into operation as the wire is driven;
a sheath pulling unit for pulling the sheath in a proximal direction, wherein the sheath pulling unit includes a sheath pulling driving unit for driving the sheath to pull the sheath;
a sheath lock unit for engaging with the sheath such that the sheath pulling unit can pull the sheath in the proximal direction;
a sheath lock driving unit for driving the sheath lock unit in such a way as to engage with the sheath; and
a controller comprising hardware, the controller being configured to control the sheath pulling driving unit and the sheath lock driving unit depending on a state of the sheath.

2. A medical instrument according to claim 1, wherein the sheath pulling unit includes a biasing member for biasing the sheath to pull the sheath.

3. A medical instrument according to claim 1, further comprising:
a sheath tension measuring unit for measuring a tension of the sheath,
wherein the controller is further configured to drive the sheath lock driving unit to lock the sheath in place when a measurement from the sheath tension measuring unit is greater than a predetermined threshold value.

4. A medical instrument according to claim 3, wherein the controller is further configured to drive the sheath pulling driving unit, disengage the sheath pulling driving unit depending on a measurement from the sheath tension measuring unit, and drives the sheath lock driving unit to lock the sheath in place.

5. A medical instrument according to claim 3, wherein the controller is further configured to drive the sheath lock driving unit to lock the sheath in place, and then drives the sheath pulling driving unit to disengage the sheath pulling driving unit depending on a measurement from the sheath tension measuring unit.

6. A medical instrument according to claim 1, wherein the sheath pulling unit includes a wire pulling unit that is capable of pulling the wire such that the sheath can be pulled by the thus pulled wire.

7. A medical instrument according to claim 6, wherein the wire pulling unit includes a wire path changing unit that changes a path taken by the wire coupled to and pulled by the wire driving unit.

8. A medical instrument according to claim 6, further comprising
a sheath tension measuring unit for measuring a tension of the sheath,
wherein the control unit drives the sheath lock driving unit when a measurement from the sheath tension measuring unit is greater than a predetermined threshold value.

9. A medical instrument according to claim 6, further comprising
a sheath displacement measuring unit for measuring a displacement of the sheath
and
a wire displacement measuring unit for measuring a displacement of the wire,
wherein the control unit drives the sheath lock driving unit depending on a rate of change in a sheath displacement, as measured by the sheath displacement measuring unit, with respect to a wire displacement as measured by the wire displacement measuring unit.

10. A medical instrument according to claim 6, further comprising
a sheath displacement measuring unit for measuring a displacement of the sheath
and
a wire displacement measuring unit for measuring a displacement of the wire,
wherein the control unit drives the sheath lock driving unit depending on a difference between a wire displacement as measured by the wire displacement measuring unit and a sheath displacement as measured by the sheath displacement measuring unit.

11. A medical instrument according to claim 6, further comprising a wire tension measuring unit for measuring a tension of the wire,
wherein the control unit drives the sheath lock driving unit when a measurement as measured by the wire tension measuring unit is greater than a predetermined threshold value.

12. A medical instrument according to claim 6, further comprising
a wire displacement measuring unit for measuring a displacement of the wire
and
a wire tension measuring unit for measuring a tension of the wire,
wherein the control unit drives the sheath lock driving unit depending on a rate of change in a wire tension, as measured by the wire tension measuring unit, with respect to a wire displacement as measured by the wire displacement measuring unit.

13. A medical instrument according to claim 1
wherein the passive unit and the wire driving unit are detachable from each other, and upon attachment of the passive unit to the wire driving unit, the sheath lock unit engages with the sheath.

14. A medical system that a medical instrument according to claim 1 is an endoscope including a viewing optical system, an imaging device and a lighting optical system, and the passive unit is defined by a distal-end portion of the endoscope to which one end of the wire is attached and a flexible portion through which the wire and the sheath are inserted, the medical system further comprising:
- a handle for driving the wire driving unit, to which the other end of the wire is attached, to put the distal-end portion and the flexible portion into operation;
- a display for displaying an image acquired through the endoscope; and
- a system controller comprising hardware, the system controller being configured to put the handle into operation thereby controlling the endoscope and permitting the image acquired through the endoscope to be displayed on the display.

15. A medical system that a medical instrument according to claim 1 is defined by a treatment tool for applying treatments to a subject of interest, and the passive unit is defined by a distal end of the treatment tool to which one end of the wire is attached and a flexible portion through which the wire and the sheath are inserted, the medical system further comprising:
- a handle for driving the wire driving unit, to which the other end of the wire is attached, to put the distal end and the flexible portion into operation;
- an endoscope including a viewing optical system an imaging device and a lighting optical system;
- a display for displaying an image acquired through the endoscope;
- and
- a system controller comprising hardware, the system controller being configured to control the treatment tool by operation of the handle and permitting the image acquired through the endoscope to be displayed on the display.

16. A medical system according to claim 15, wherein the treatment tool is inserted through the endoscope.

* * * * *